United States Patent
Gonzales et al.

(10) Patent No.: US 10,457,676 B2
(45) Date of Patent: Oct. 29, 2019

(54) CAPSAZEPINE ANALOGS FOR THE TREATMENT OF CANCER AND OTHER PROLIFERATIVE DISEASES

(71) Applicant: THE BOARD OF REGENTS OF THE UNIVERSITY OF TEXAS SYSTEM, Austin, TX (US)

(72) Inventors: Cara B. Gonzales, San Antonio, TX (US); Stanton McHardy, Helotes, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/505,260

(22) PCT Filed: Aug. 25, 2015

(86) PCT No.: PCT/US2015/046784
§ 371 (c)(1),
(2) Date: Feb. 21, 2017

(87) PCT Pub. No.: WO2016/033105
PCT Pub. Date: Mar. 3, 2016

(65) Prior Publication Data
US 2017/0275280 A1    Sep. 28, 2017

Related U.S. Application Data

(60) Provisional application No. 62/043,750, filed on Aug. 29, 2014.

(51) Int. Cl.
| | | |
|---|---|---|
| C07D 471/04 | (2006.01) |
| A61K 31/55 | (2006.01) |
| C07D 233/16 | (2006.01) |
| A61K 31/472 | (2006.01) |
| C07D 209/44 | (2006.01) |
| A61K 31/5377 | (2006.01) |
| C07D 213/68 | (2006.01) |
| A61K 31/4745 | (2006.01) |
| A61K 31/17 | (2006.01) |
| A61K 45/06 | (2006.01) |
| A61K 31/155 | (2006.01) |
| A61K 31/165 | (2006.01) |
| A61K 31/4035 | (2006.01) |
| C07D 217/06 | (2006.01) |
| C07D 223/16 | (2006.01) |
| C07C 275/24 | (2006.01) |
| C07C 211/29 | (2006.01) |
| C07C 335/12 | (2006.01) |
| C07C 233/29 | (2006.01) |
| A61P 35/00 | (2006.01) |

(52) U.S. Cl.
CPC .......... *C07D 471/04* (2013.01); *A61K 31/155* (2013.01); *A61K 31/165* (2013.01); *A61K 31/17* (2013.01); *A61K 31/4035* (2013.01); *A61K 31/472* (2013.01); *A61K 31/4745* (2013.01); *A61K 31/5377* (2013.01); *A61K 31/55* (2013.01); *A61K 45/06* (2013.01); *A61P 35/00* (2018.01); *C07C 211/29* (2013.01); *C07C 233/29* (2013.01); *C07C 275/24* (2013.01); *C07C 335/12* (2013.01); *C07D 209/44* (2013.01); *C07D 213/68* (2013.01); *C07D 217/06* (2013.01); *C07D 223/16* (2013.01)

(58) Field of Classification Search
CPC ..... C07D 471/04; A61P 35/00; A61K 31/155; A61K 31/165; A61K 31/17; A61K 31/4035; A61K 31/472; A61K 31/4745; A61K 31/5377; A61K 31/55
USPC ........................................................ 514/213
See application file for complete search history.

(56) References Cited

U.S. PATENT DOCUMENTS

| 5,637,619 A | 6/1997 | Sartorelli et al. |
| 5,981,521 A | 11/1999 | Haviv et al. |
| 2005/0070570 A1 | 3/2005 | Garcia et al. |
| 2005/0165004 A1 | 7/2005 | Skogvall et al. |

(Continued)

FOREIGN PATENT DOCUMENTS

| CN | 101791312 | 8/2010 |
| EP | 0671389 | 9/1995 |

(Continued)

OTHER PUBLICATIONS

Arroyo et al. Eur. J. Org. Chem. (2014), 26, p. 5720-5727.*

(Continued)

*Primary Examiner* — Yong L Chu
(74) *Attorney, Agent, or Firm* — Parker Highlander PLLC

(57) ABSTRACT

The present disclosure relates generally to derivatives of capsazepine and methods of use thereof In some aspects, the present disclosure relates to using capsazepine derivatives to treat cancer or other hyperproliferative diseases. In some aspects of the present disclosure, the disclosure provides capsazepine derivatives which may be useful in the treatment of cancer. Such cancers that the compounds may be used to treating include but are not limited to breast, cervical, oral, head, neck, or prostate cancer. In some aspects, the compounds may be useful in treating a tumor by direct injection of the compound into the tumor, particularly an oral tumor. In other aspects, the compounds are administered systemically. The compounds of the present disclosure may also be used to treat the pain associated with a tumor for which it is being administered.

20 Claims, 6 Drawing Sheets

(56) References Cited

U.S. PATENT DOCUMENTS

| | | |
|---|---|---|
| 2006/0040919 A1 | 2/2006 | Skogvall et al. |
| 2012/0122842 A1 | 5/2012 | Curtin et al. |
| 2012/0220572 A1 | 8/2012 | Tong et al. |
| 2013/0109685 A1* | 5/2013 | Aissaoui ............ A71K 31/4035 514/230.5 |
| 2014/0004243 A1 | 1/2014 | Tahara et al. |

FOREIGN PATENT DOCUMENTS

| | | |
|---|---|---|
| WO | WO 2017/063491 | 4/1917 |
| WO | WO 2000/056681 | 9/2000 |
| WO | WO 2001/014328 | 3/2001 |
| WO | WO 2007/011290 | 1/2007 |
| WO | WO 2007/107352 | 9/2007 |
| WO | WO 2007/117053 | 10/2007 |
| WO | WO 2008/130321 | 10/2008 |
| WO | WO 2009/073203 | 6/2009 |
| WO | WO 2010/114824 | 10/2010 |
| WO | WO 2012/121273 | 9/2012 |
| WO | WO 2012/164118 | 12/2012 |
| WO | WO 2014/089067 | 6/2014 |

OTHER PUBLICATIONS

Gonzales et al., "Vanilloids induce oral cancer apoptosis independent of TRPV1," *Oral Oncology*, 50:437-447, 2014.

PCT International Invitation to Pay Additional Fees issued in International Application No. PCT/US2015/046784, dated Nov. 2, 2015.

PCT International Search Report and Written Opinion issued in International Application No. PCT/US2015/046784, dated Jan. 8, 2016.

PUBCHEM, Substance Record for SID 141197007, Create Date: Aug. 20, 2012. Retrieved from the Internet on Oct. 1, 2015 at <URL:https://pubchem.ncbi.nlm.nih.gov/substance/141197007#section=Top>.

PUBCHEM, Substance Record for SID 59425298, Create Date: May 25, 2009. Retrieved from the Internet on Nov. 12, 2015 at <URL:https://pubchem.ncbi.nlm.nih.gov/substance/5942598#section=Top>.

Arroyo et al., "One-pot α-amido-sulfone-mediated variation of the Pictet-Spengler tetrahydroisoquinoline synthesis, suitable for amide-type substrates," *European Journal of Organic Chemistry*, 2014(26):5720-5727, 2014.

Berglund et al., "SAR studies of capsazepinoid bronchodilators 3: The thiourea part (coupling region) and the 2-(4-chlorophenyl)ethyl moiety (C-region)," *Bioorganic & Medicinal Chemistry*, 16(5):2529-2540, 2008.

Berglund et al., "SAR studies of capsazepinoid bronchodilators. Part 2: Chlorination and catechol replacement in the A-ring," *Bioorganic & Medicinal Chemistry*, 16(5):2513-2528, 2008.

Booth et al., "Dibenzoquinazoline phosphodiesterase diones as antihypertensive cyclic guanosine monophosphate phosphodiesterase inhibitors," *Biochemical Pharmacology*, 36(20):3517-21, 1987.

Busato et al., "New N-acyl, N-alkyl, and N-bridged derivatives of rac-6,6',7,7'-tetramethoxy-1,1',2,2',3,3',4,4'-octahydro-1,1'-bisisoquinoline," *Tetrahedron*, 59(4):461-472, 2003.

Chen et al., "Alkaloids from trunk bark of Hernandia nymphaefolia," *Phytochemistry*, 42(5):1479-1474, 1996.

Chen et al., "Anti-platelet aggregation alkaloids and lignans from Hernandia nymphaeifolia," *Planta Medica*, 66(3):251-256, 2000.

Chen et al., "New dimeric aporphine alkaloids and cytotoxic constituents of Hernandia nymphaeifolia," *Planta Medica*, 62(6):528-533, 1996.

Chen et al., "Vasorelaxing and antioxidant constituents from Hernandia nymphaeifolia," *Planta Medica*, 67(7):593-598, 2001.

Craig et al., "Structural Studies of N-Acyl 1,1'-Bis(1,2,3,4-tetrahydroisoquinoline) Derivatives," *Australian Journal of Chemistry*, 55(11):733-736, 2002.

Dalence-Guzman et al., "SAR studies of capsazepinoid bronchodilators. Part 1: The importance of the catechol moiety and aspects of the B-ring structure," *Bioorganic & Medicinal Chemistry*, 16(5):2499-2512, 2008.

De Petrocellis et al., "Tetrahydroisoquinoline-Derived Urea and 2,5-Diketopiperazine Derivatives as Selective Antagonists of the Transient Receptor Potential Melastatin 8 (TRPM8) Channel Receptor and Antiprostate Cancer Agents," *Journal of Medicinal Chemistry*, 59(12):5661-5683, 2016. With correction to publication: *Journal of Medicinal Chemistry*, 59(16):7697, 2016.

Kaur et al., "Synthesis and antispasmodic activity evaluation of bis-(papaverine) analogues," *Chemical & Pharmaceutical Bulletin*, 52(3):316-321, 2004.

Kim, "3-D-QSAR analysis of N-(3-acyloxy-2-benzylpropyl)-N'-dihydroxytetrahydrobenzazepine and tetrahydroisoquinoline and N-(3-acyloxy-2-benzylpropyl)-N'-(4-hydroxy-3-methoxybenzyl) thioureas analogues as potent vanilloid receptor ligands," *Bioorganic & Medicinal Chemistry*, 10(5):1367-1372, 2002.

Klopman et al., "Quantitative structure-agonist activity relationship of capsaicin analogues," *Journal of Computer-Aided Molecular Design*, 9(3):283-94, 1995.

Lal et al., "Trequinsin, a potent new antihypertensive vasodilator in the series of 2-(arylimino)-3-alkyl-9,10-dimethoxy-3,4,6,7-tetrahydro-2H-py rim ido [6,1-a]isoquinolin-4-ones," *Journal of Medicinal Chemistry*, 27(11):1470-80, 1984.

Lenz, "The synthesis of pyrimidoaporphines," *Tetrahedron*, 40(20):4003-12, 1984.

Mahmutovic-Persson et al., "Capacity of capsazepinoids to relax human small airways and inhibit TLR3-induced TSLP and IFNβ production in diseased bronchial epithelial cells," *International Immunopharmacology*, 13(3):292-300, 2012.

Mihalyi et al., "Synthesis and multidrug resistance reversal activity of 1,2-disubstituted tetrahydroisoquinoline derivatives," *Anticancer Research*, 24(3A):1631-1636, 2004.

Osante et al., "Stereodivergent synthesis of hetero-fused isoquinolines by acyliminium and metallation methods," *European Journal of Organic Chemistry*, 7:1267-1277, 2001.

Shono et al., "Cerasoidine, a Bis-aporphine Alkaloid Isolated from Polyalthia cerasoides during Screening for Wnt Signal Inhibitors," *Journal of Natural Products*, 79(8):2083-2088, 2016.

Skogvall et al., "Discovery of a potent and long-acting bronchorelaxing capsazepinoid, RESPIR 4-95," *Pulmonary Pharmacology & Therapeutics*, 21(1):125-133, 2008.

Skogvall et al., "Effects of capsazepine on human small airway responsiveness unravel a novel class of bronchorelaxants," *Pulmonary Pharmacology & Therapeutics*, 20(3):273-280, 2007.

Walpole et al., "The discovery of capsazepine, the first competitive antagonist of the sensory neuron excitants capsaicin and resiniferatoxin," *Journal of Medicinal Chemistry*, 37(13):194-254, 1994.

Chen et al., "Blockade of STAT3 activation by sorafenib derivatives through enhancing SHP-1 phosphatase activity," *European Journal of Medicinal Chemistry*, 55:220-227, 2012.

Kim et al., "Induction of caspase-dependent apoptosis in melanoma cells by the synthetic compound (E)-1-(3,4-dihydroxyphenethyl)-3-styrylurea," *BMB Reports*, 42(12):806-811, 2009.

Partial Supplementary European Search Report issued in European Patent Application No. 15836811.8, dated Apr. 20, 2018.

De La Chapa et al., "Synthesis and SAR of novel capsazepine analogs with significant anti-cancer effects in multiple cancer types," *Bioorganic & Medicinal Chemistry*, 27(1):208-215, 2019.

Horne et al., "Optimization of potency and pharmacokinetic properties of tetrahydroisoquinoline transient receptor potential melastatin 8 (TRPM8) antagonists," *Journal of Medicinal Chemistry*, 57(7):2989-3004, 2014.

Ivanov et al., "Synthesis and contractile activity of substituted 1,2,3,4-tetrahydroisoquinolines," *Molecules Online*, 16(8):7019-7042, 2011.

Partial Supplementary European Search Report issued in European Patent Application No. 1915216.1, dated Aug. 9, 2019.

Shukla et al., "QSAR and docking studies on capsazepine derivatives for immunomodulatory and anti-inflammatory activity," *PLoS One*, 9(7):e100797, 2014.

(56) References Cited

OTHER PUBLICATIONS

Yan et al., "High-throughput screening assay for new ligands at human melatonin receptors," *Acta Pharmacologica Sinica*, 29(12):1515-1521, 2008.

* cited by examiner

CAPSAZEPINE ANALOGS FOR THE TREATMENT OF CANCER AND OTHER PROLIFERATIVE DISEASES

This application is a national phase application under 35 U.S.C. § 371 of International Application No. PCT/US2015/046784, filed Aug. 25, 2015, which claims benefit of priority to U.S. Provisional Application Ser. No. 62/043,750, filed Aug. 29, 2014, all contents of each are hereby incorporated by reference.

BACKGROUND

I. Field

The present disclosure relates generally to novel capsazepine derivatives, their use in pharmaceutical compositions, methods of using the compounds for treating diseases.

II. Description of Related Art

Advanced oral cancer has a 70% death rate that has not changed in over 30 years. Furthermore, the pain associated with inoperable oral cancer is reported to be the worst symptom by these patients and there are no drugs available that effectively alleviate this pain. Patients with inoperable tumors in the head and neck experience intense pain as the tumor continues to grow and invade critical structures. Opioids are the main drugs used to manage pain and to provide palliative care, however these patients quickly develop tolerance to these drugs resulting in little to no pain management and a very slow and painful death. As these tumors grow they frequently invade neurovascular structures resulting in intense pain and they often rupture the carotid artery resulting in death. Reduction in tumor volume and blockage of TRPV1 channels not only prevents invasion of critical structures but also provides a better quality of life and may prove useful in palliative care for patients undergoing treatment and patients at end-of-life. Oral cancer patients' tumors are accessible and frequently are inoperable because they invade or are approximated upon critical structures in the head and neck. Many oral cancer patients die from tumor invasion of the carotid artery. This leaves no treatment options for this patient population. Administering capsazepine, especially direct injection of capsazepine into these tumors, results in reduction of tumor volume and can prevent tumor invasion of nerve bundles and critical structures such as the carotid artery (WO 2014/089067). The development of additional compounds to treat these cancers and other cancers represents an important clinical challenge.

SUMMARY

In accordance with the present disclosure, there is provided a method of treating cancer comprising administering to a patient in need thereof a therapeutically effective amount of a compound of the formula:

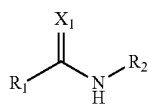
(I)

wherein $X_1$ is O or S; $R_1$ is $—NR_3R_4$, wherein $R_3$ is hydrogen, alkyl$_{(C≤12)}$, substituted alkyl$_{(C≤12)}$; and $R_4$ is aralkyl$_{(C≤12)}$ or substituted aralkyl$_{(C≤12)}$; or

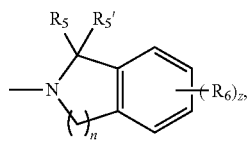

wherein $R_5$ and $R_{5'}$ are each independently hydrogen, or alkyl$_{(C≤12)}$, alkenyl$_{(C≤12)}$, alkynyl$_{(C≤12)}$, aryl$_{(C≤12)}$, aralkyl$_{(C≤12)}$ or a substituted version of any of these groups; n is 0, 1, 2, 3, 4, 5, or 6; $R_6$ is hydrogen, halo, amino, cyano, hydroxy, mercapto, nitro, or sulfo, or alkyl$_{(C≤12)}$, aryl$_{(C≤12)}$, alkoxy$_{(C≤12)}$, alkylamino$_{(C≤12)}$, dialkylamino$_{(C≤12)}$, alkylsulfonylamino$_{(C≤12)}$, alkylsulfonyl$_{(C≤12)}$, or a substituted version of any of these groups; and z is 0, 1, 2, 3, 4, or 5; $R_2$ is alkenyl$_{(C≤12)}$, aralkyl$_{(C≤12)}$, or a substituted version of either of these groups; or a compound of the formula:

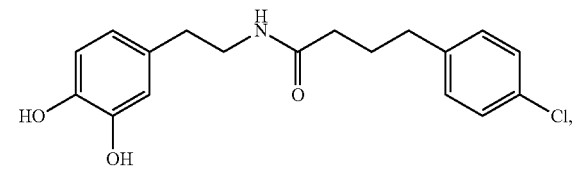

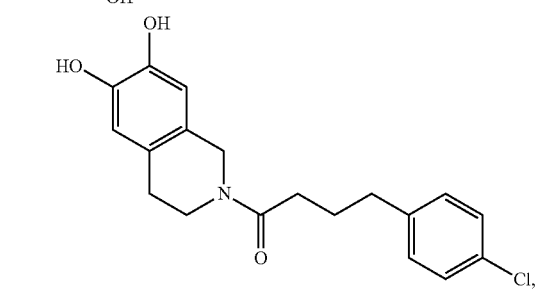

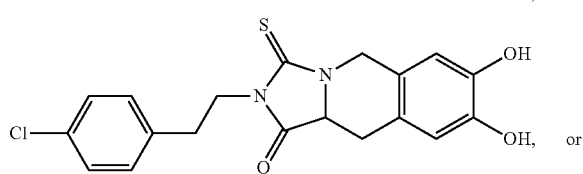

or

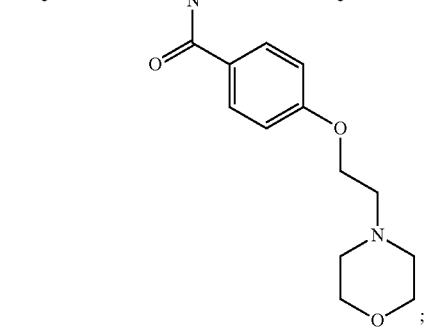

;

provided that the compound is not of the formula:

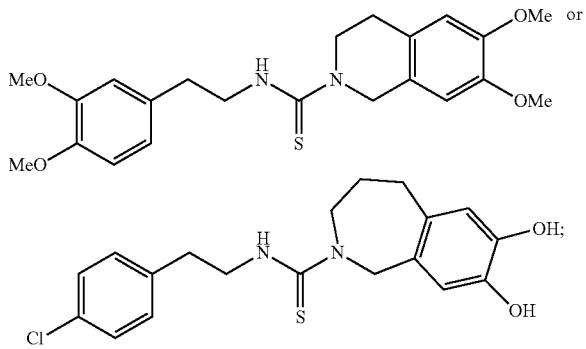

or a pharmaceutically acceptable salt or tautomer thereof. In some embodiments, $X_1$ is O. In other embodiments, $X_1$ is S. In some embodiments, $R_1$ is $-NR_3R_4$, wherein: $R_3$ is hydrogen, alkyl$_{(C\leq12)}$, substituted alkyl$_{(C\leq12)}$; and $R_4$ is aralkyl$_{(C\leq12)}$ or substituted aralkyl$_{(C\leq12)}$. In some embodiments, $R_3$ is hydrogen. In other embodiments, $R_3$ is alkyl$_{(C\leq12)}$. In some embodiments, $R_3$ is alkyl$_{(C\leq12)}$. In some embodiments, $R_3$ is methyl. In some embodiments, $R_4$ is aralkyl$_{(C\leq12)}$. In some embodiments, $R_4$ is benzyl or 2-phenylethyl. In some embodiments, $R_4$ is substituted aralkyl$_{(C\leq12)}$. In some embodiments, $R_4$ is 3,4-dihydroxybenzyl, 4-chlorobenzyl, 4-fluorobenzyl, 2,4-dichlorobenzyl, 3,4-dimethoxybenzyl, 2-(3,4-dihydroxyphenyl)ethyl, 2-(4-chlorophenyl)ethyl, 2-(4-fluorophenyl)ethyl, 2-(2,4-dichlorophenyl)ethyl, or 2-(dimethoxyphenyl)ethyl. In other embodiments, $R_1$ is

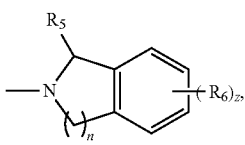

wherein: $R_5$ and $R_{5'}$ are each independently hydrogen, alkyl$_{(C\leq12)}$, alkenyl$_{(C\leq12)}$, alkynyl$_{(C\leq12)}$, aryl$_{(C\leq12)}$, aralkyl$_{(C\leq12)}$ or a substituted version of any of these groups; n is 0, 1, 2, 3, 4, 5, or 6; $R_6$ is hydrogen, halo, amino, cyano, hydroxy, mercapto, nitro, or sulfo, or alkyl$_{(C\leq12)}$, aryl$_{(C\leq12)}$, alkoxy$_{(C\leq12)}$, alkylamino$_{(C\leq12)}$, dialkylamino$_{(C\leq12)}$, alkylsulfonylamino$_{(C\leq12)}$, alkylsulfonyl$_{(C\leq12)}$, or a substituted version of any of these groups; and z is 0, 1, 2, 3, 4, or 5. In some embodiments, $R_5$ is hydrogen. In other embodiments, $R_5$ is alkyl$_{(C\leq12)}$. In some embodiments, $R_5$ is alkyl$_{(C\leq8)}$. In some embodiments, $R_5$ is isopropyl. In some embodiments, $R_{5'}$ is hydrogen. In other embodiments, $R_{5'}$ is alkyl$_{(C\leq6)}$. In some embodiments, $R_{5'}$ is methyl. In other embodiments, $R_5$ is aryl$_{(C\leq12)}$. In some embodiments, $R_5$ is phenyl. In some embodiments, n is 0, 1, 2, 3, or 4. In some embodiments, n is 1, 2, or 3. In some embodiments, n is 1. In other embodiments, n is 2. In other embodiments, n is 3. In some embodiments, $R_6$ is hydrogen, halo, amino, hydroxy, or alkyl$_{(C\leq12)}$, alkoxy$_{(C\leq12)}$, alkylamino$_{(C\leq12)}$, dialkylamino$_{(C\leq12)}$, or a substituted version of any of these groups. In some embodiments, $R_6$ is hydroxy. In other embodiments, $R_6$ is halo. In other embodiments, $R_6$ is alkoxy$_{(C\leq12)}$. In some embodiments, $R_6$ is alkoxy$_{(C\leq8)}$. In some embodiments, $R_6$ is methoxy. In some embodiments, z is 0, 1, 2, or 3. In some embodiments, z is 1 or 2. In some embodiments, z is 1. In other embodiments, z is 2. In some embodiments, $R_2$ is alkenyl$_{(C\leq12)}$. In some embodiments, $R_2$ is alkenyl$_{(C\leq8)}$. In some embodiments, $R_2$ is 2-propenyl. In other embodiments, $R_2$ is aralkyl$_{(C\leq12)}$. In some embodiments, $R_2$ is aralkyl$_{(C\leq8)}$. In some embodiments, $R_2$ is benzyl or 2-phenylethyl. In other embodiments. $R_2$ is substituted aralkyl$_{(C\leq12)}$. In some embodiments, $R_2$ is substituted aralkyl$_{(C\leq8)}$. In some embodiments, $R_2$ is 3,4-dihydroxybenzyl, 4-chlorobenzyl, 4-fluorobenzyl, 2,4-dichlorobenzyl, 3,4-dimethoxybenzyl, 2-(3,4-dihydroxyphenyl)ethyl, 2-(4-chlorophenyl)ethyl, 2-(4-fluorophenyl)ethyl, 2-(2,4-dichlorophenyl)ethyl, or 2-(dimethoxyphenyl)ethyl. In some embodiments, the formula is further defined as:

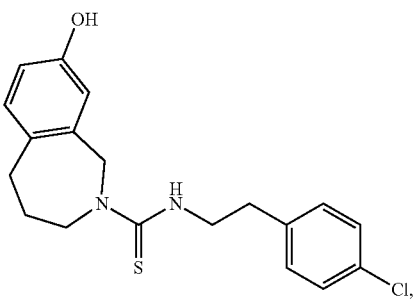

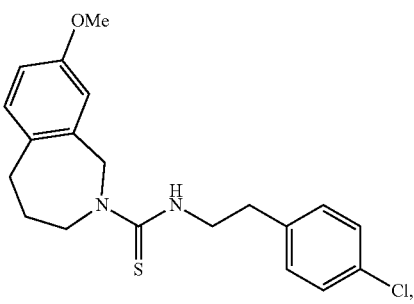

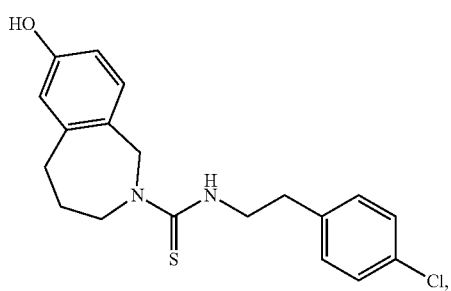

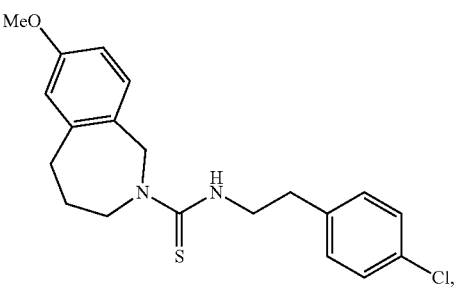

-continued
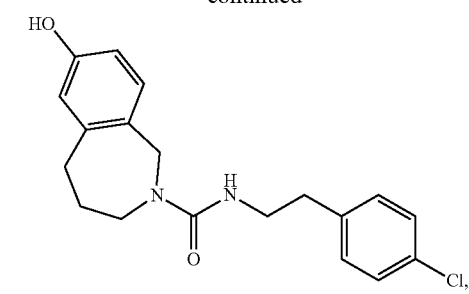
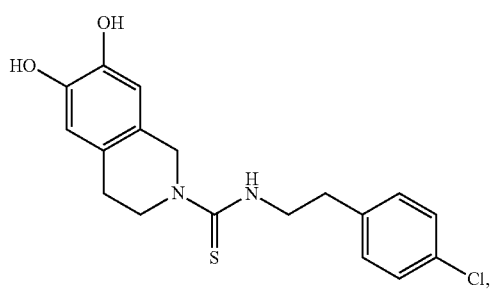
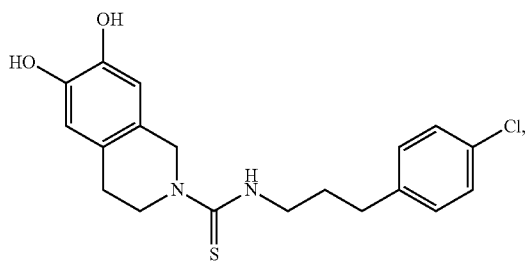
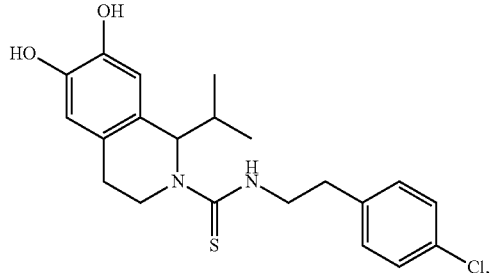
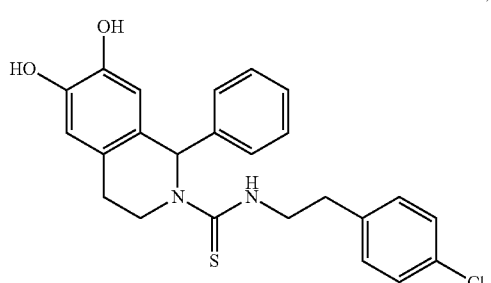
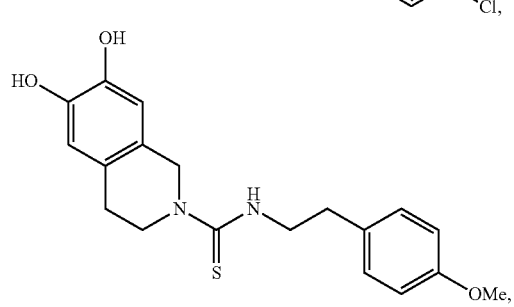
-continued
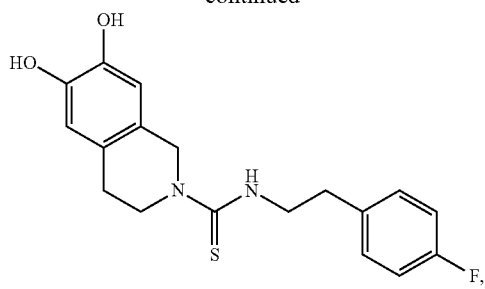
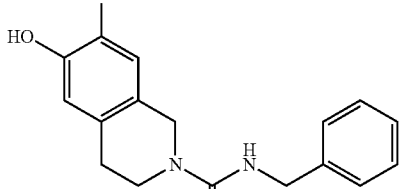
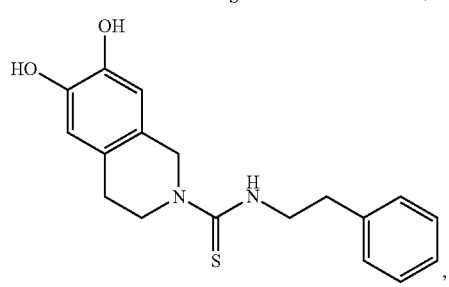
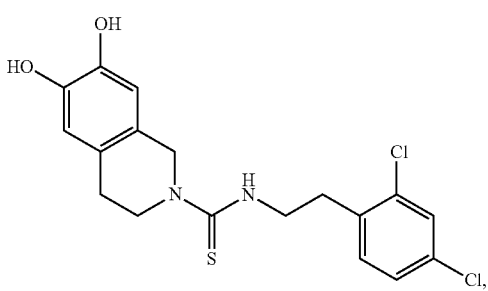
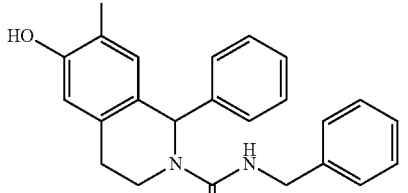
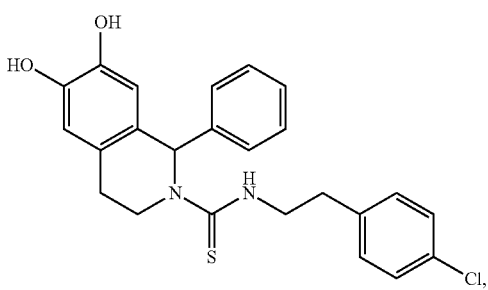

-continued
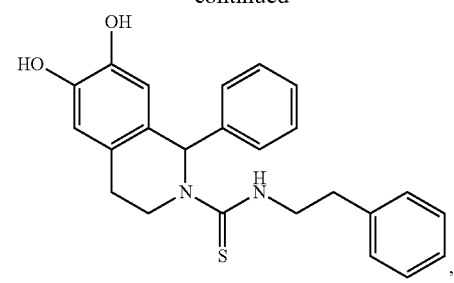
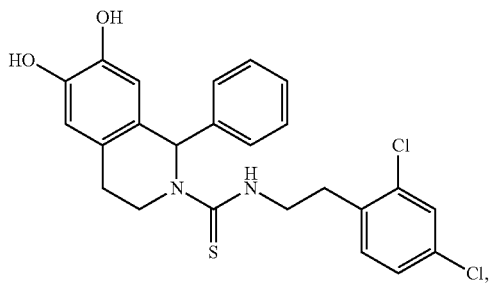
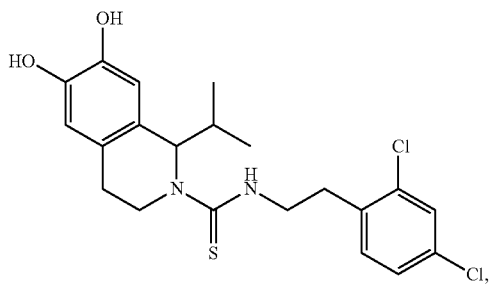
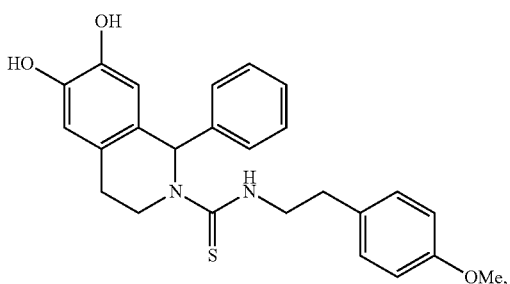
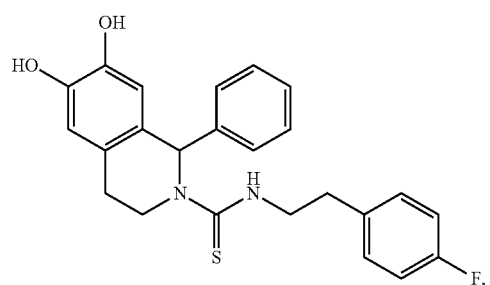
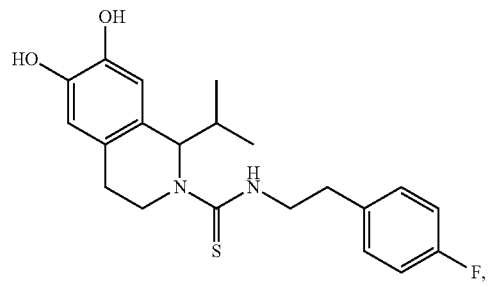
-continued
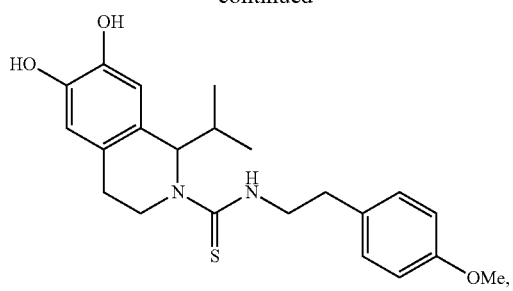
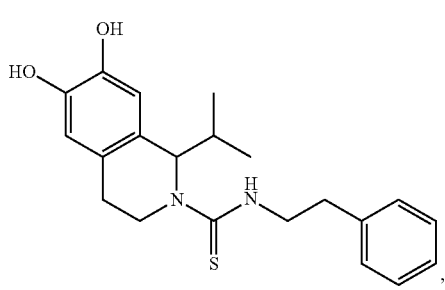
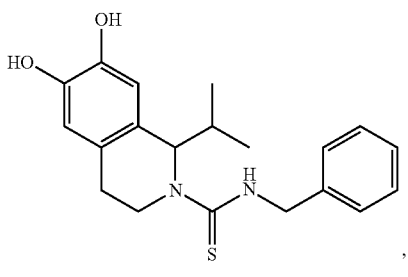
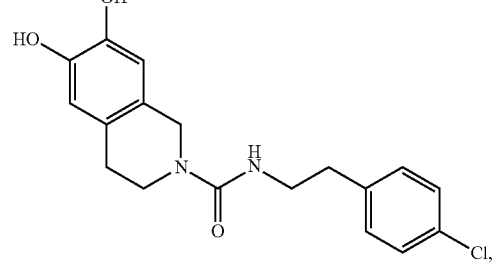
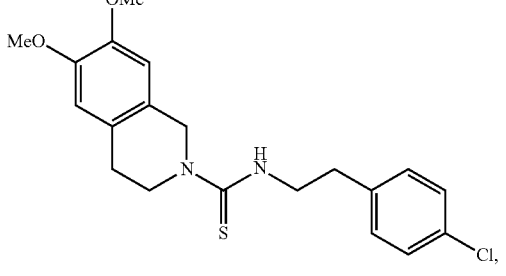
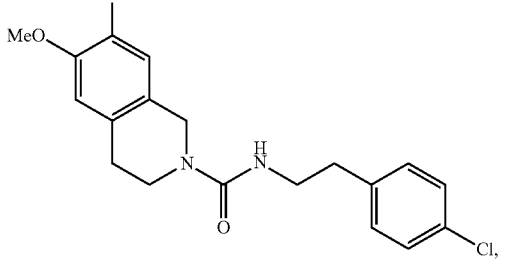

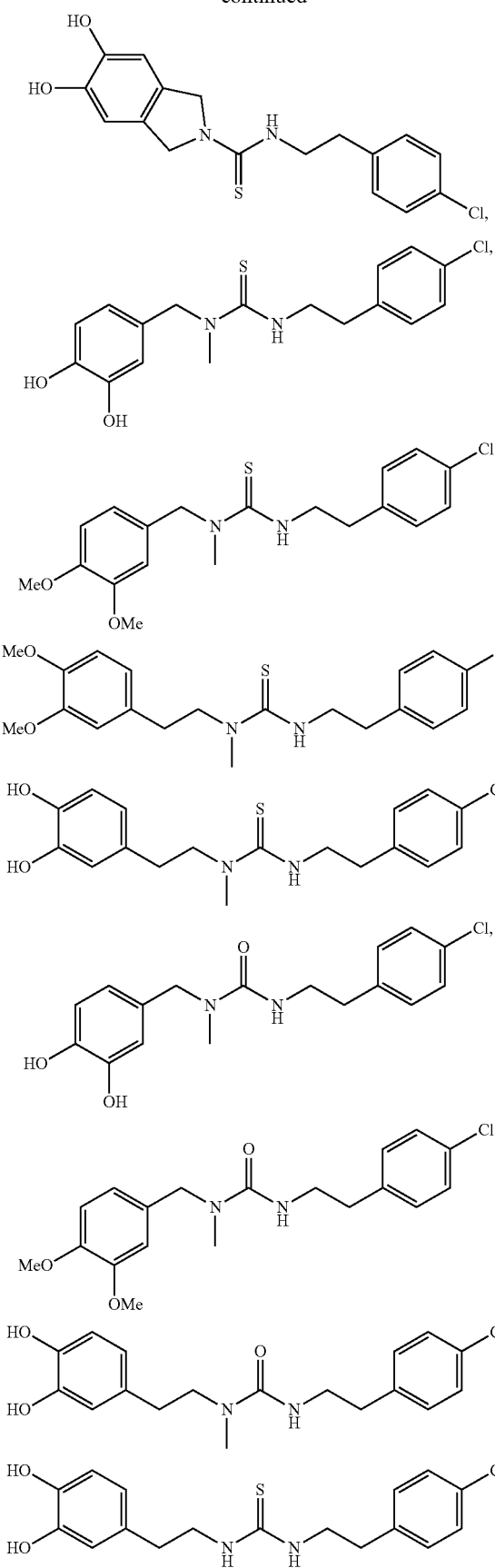
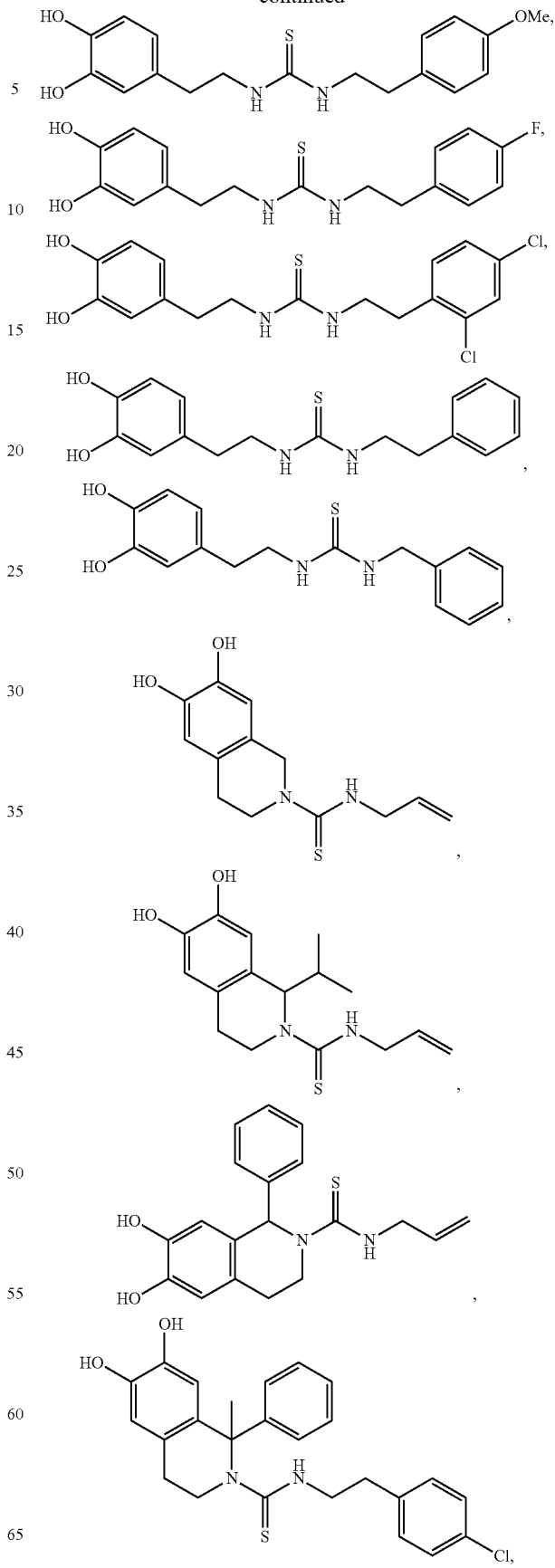

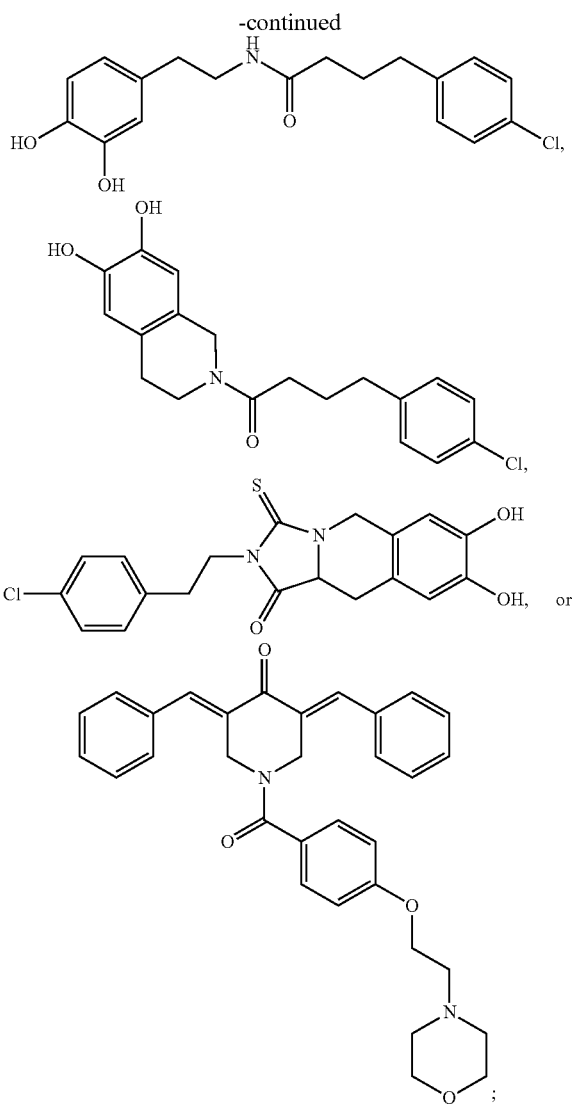

or a pharmaceutically acceptable salt or tautomer thereof. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is a cancer of the breast, prostate, cervix, head, lung, neck, oral or nasal mucosa, or a solid tumor. In some embodiments, the cancer is a cancer of the head, neck, or oral or nasal mucosa. In other embodiments, the cancer is a cancer of the breast, prostate, cervix, or lung. In some embodiments, the cancer is inoperable. In some embodiments, the inoperable cancer becomes operable after treatment with the compound. In some embodiments, the cancer is an oral squamous cell carcinoma. In some embodiments, the cancer is a solid tumor. In some embodiments, the method comprises injecting the compound directly into the tumor. In some embodiments, the compound is formulated as an injectable solution. In some embodiments, the method comprises administering the compound systemically. In some embodiments, the compound is formulated for oral or intravenous administration. In some embodiments, the method further comprises alleviating pain. In some embodiments, the method further comprises a second therapeutic agent. In some embodiments, the second therapeutic agent is surgery, radiotherapy, immunotherapy, genetic therapy, or a second chemotherapeutic compound. In some embodiments, the second therapeutic agent is metformin. In some embodiments, the compound reduces the tumor size such that the tumor becomes resectable.

In yet another aspect, the present disclosure provides a method of reducing the size of a tumor comprising administering to a patient in need thereof a therapeutically effective amount of a compound of the formula:

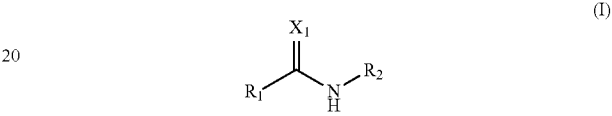

wherein $X_1$ is O or S; $R_1$ is $-NR_3R_4$, wherein $R_3$ is hydrogen, alkyl$_{(C \leq 12)}$, substituted alkyl$_{(C \leq 12)}$; and $R_4$ is aralkyl$_{(C \leq 12)}$ or substituted aralkyl$_{(C \leq 12)}$; or

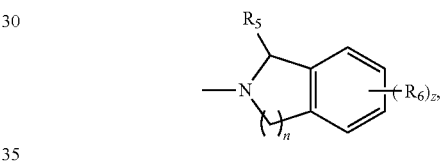

wherein $R_5$ is hydrogen, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$ or a substituted version of any of these groups; n is 0, 1, 2, 3, 4, 5, or 6; $R_6$ is hydrogen, halo, amino, cyano, hydroxy, mercapto, nitro, or sulfo, or alkyl$_{(C \leq 12)}$, aryl$_{(C \leq 12)}$, alkoxy$_{(C \leq 12)}$, alkylamino$_{(C \leq 12)}$, dialkylamino$_{(C \leq 12)}$, alkylsulfonylamino$_{(C \leq 12)}$, alkylsulfonyl$_{(C \leq 12)}$, or a substituted version of any of these groups; and z is 0, 1, 2, 3, 4, or 5; $R_2$ is alkenyl$_{(C \leq 12)}$, aralkyl$_{(C \leq 12)}$, or a substituted version of either of these groups; or a compound of the formula:

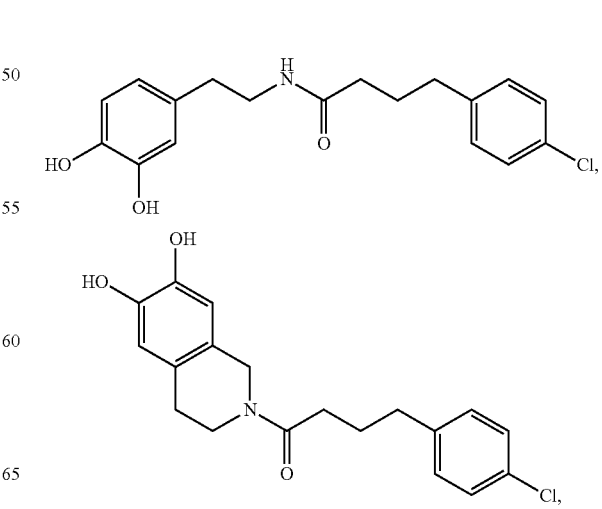

-continued

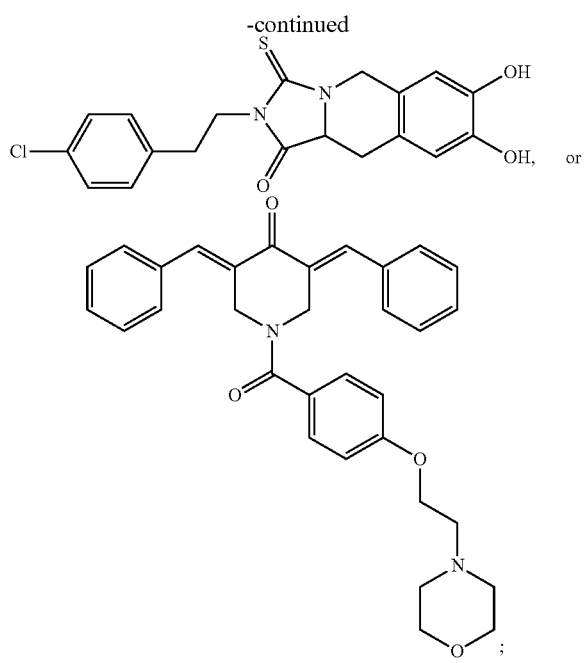

provided that the compound is not of the formula:

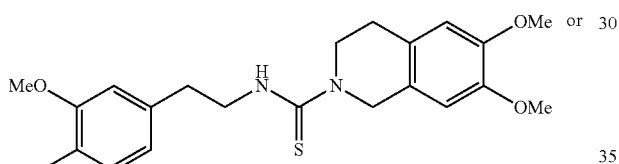

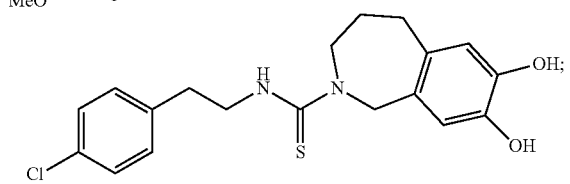

or a pharmaceutically acceptable salt or tautomer thereof.

In yet another aspect, the present disclosure provides a compound of the formula:

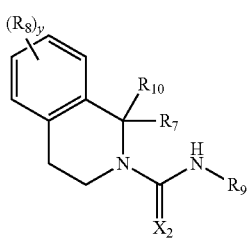

(II)

wherein $X_2$ is O or S; $R_7$ is —CH(CH$_3$)$_2$, aryl$_{(C \leq 12)}$, or substituted aryl$_{(C \leq 12)}$; $R_8$ is —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, alkyl$_{(C \leq 12)}$, or substituted alkyl$_{(C \leq 12)}$; y is 0, 1, 2, 3, 4, 5, 6, 7, 8, or 9; $R_9$ is alkenyl$_{(C \leq 12)}$, aryl$_{(C \leq 12)}$, aralkyl$_{(C \leq 12)}$, or a substituted version of either of these groups; and $R_{10}$ is hydrogen, alkyl$_{(C \leq 12)}$, or substituted alkyl$_{(C \leq 12)}$; or a pharmaceutical salt or tautomer thereof. In some embodiments, $X_2$ is S. In some embodiments, $R_7$ is aryl$_{(C \leq 12)}$ or substituted aryl$_{(C \leq 12)}$. In some embodiments, $R_{10}$ is alkyl$_{(C \leq 6)}$ or substituted alkyl$_{(C \leq 6)}$. In some embodiments, y is 0, 1, 2, 3, or 4. In some embodiments, $R_9$ is alkenyl$_{(C \leq 12)}$ or substituted alkenyl$_{(C \leq 12)}$. In some embodiments, $R_9$ is aralkyl$_{(C \leq 12)}$ or substituted aralkyl$_{(C \leq 12)}$. In some embodiments, the formula is further defined as:

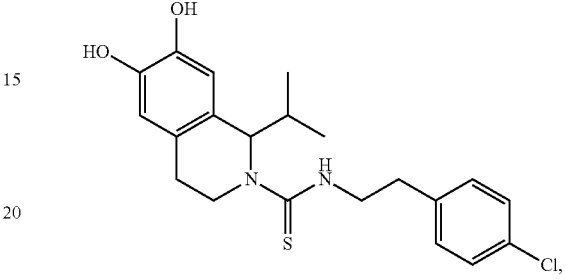

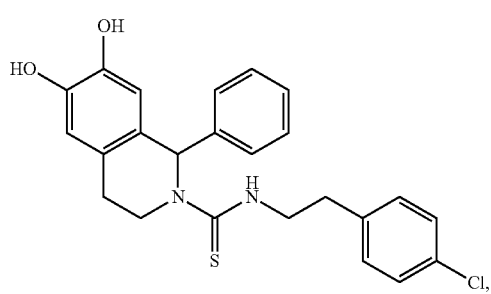

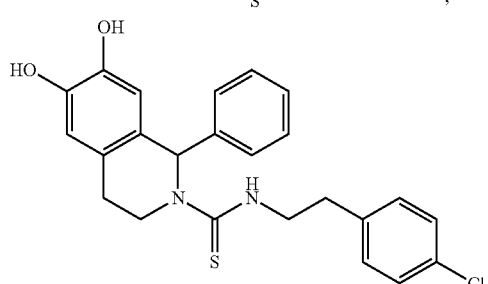

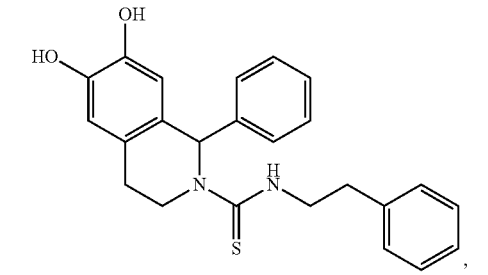

-continued
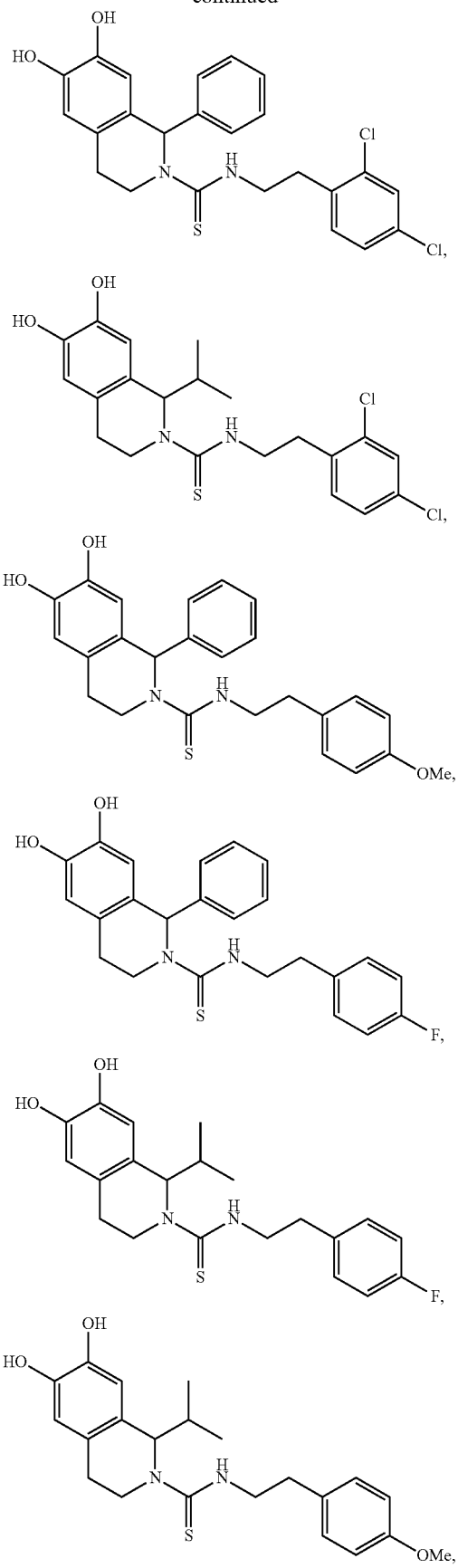
-continued
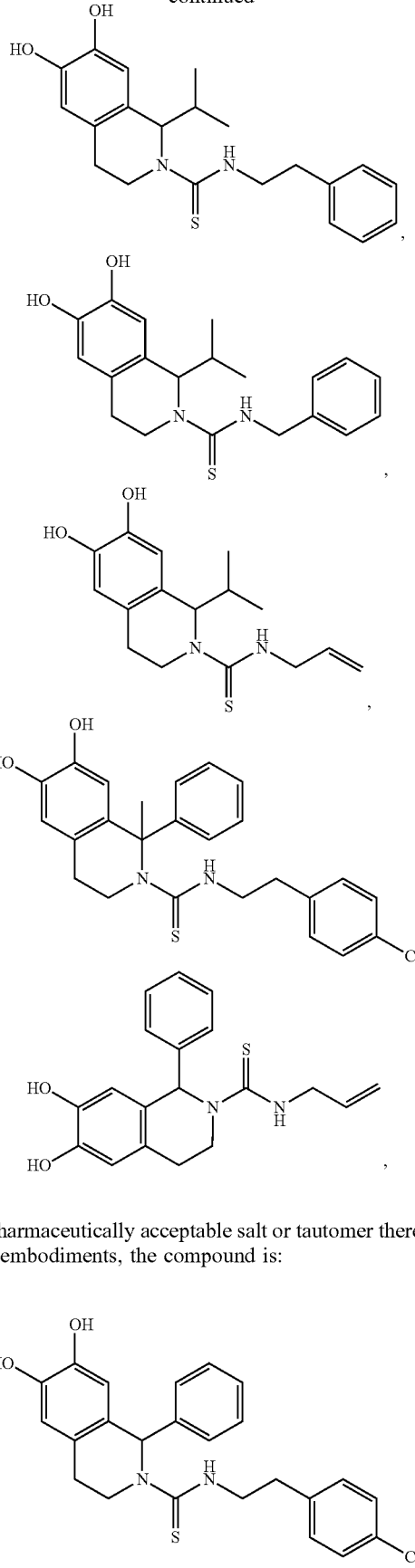
or a pharmaceutically acceptable salt or tautomer thereof. In some embodiments, the compound is:
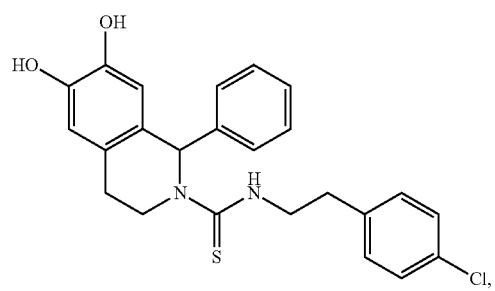

-continued
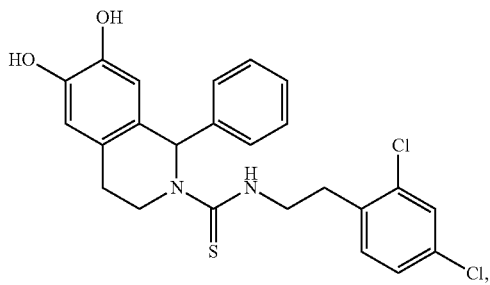
or a pharmaceutically acceptable salt or tautomer thereof.
In still another aspect, the present disclosure provides a compound of the formula:
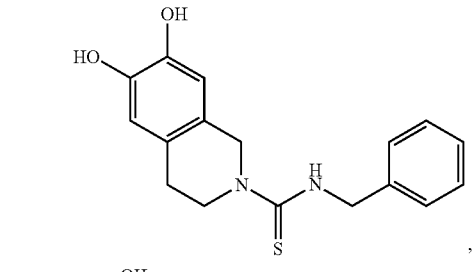
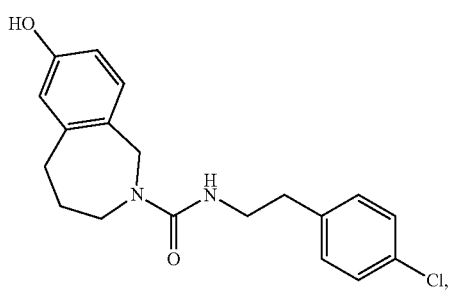
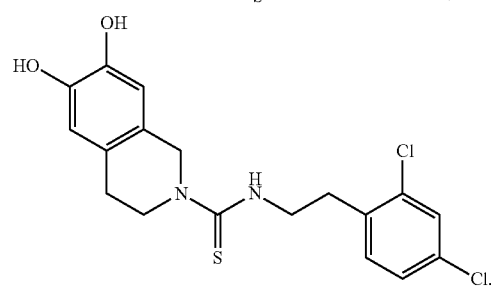
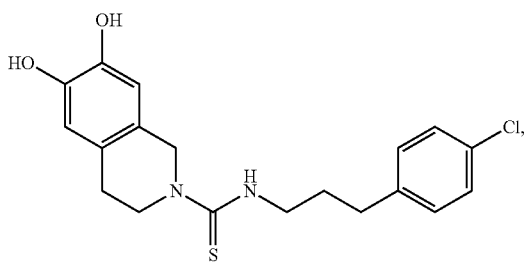
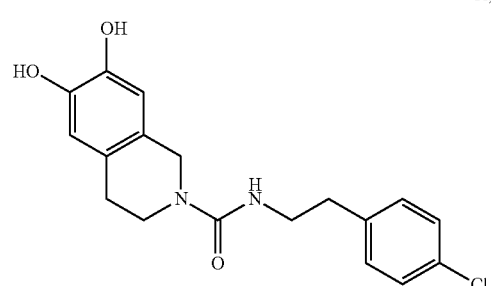
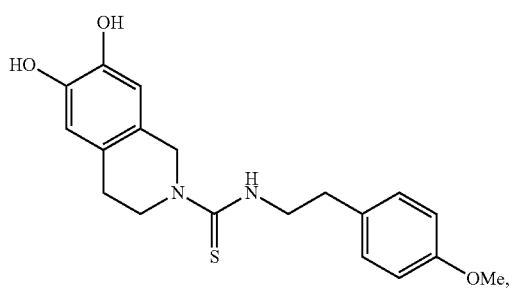
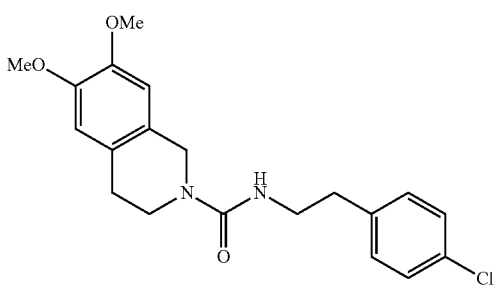
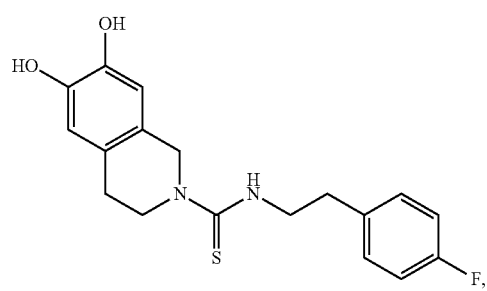
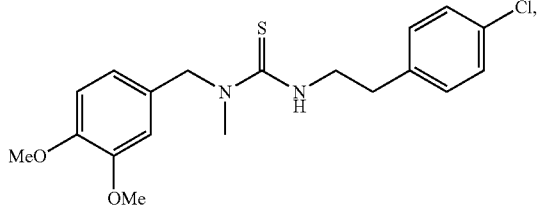

19
-continued

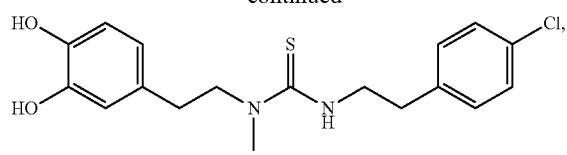
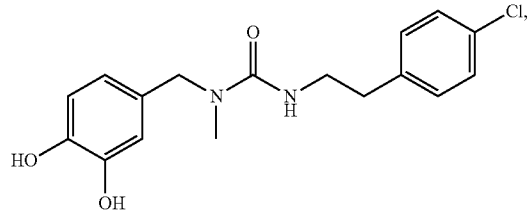
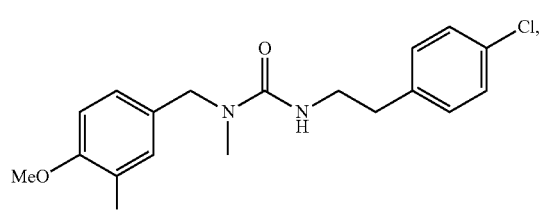
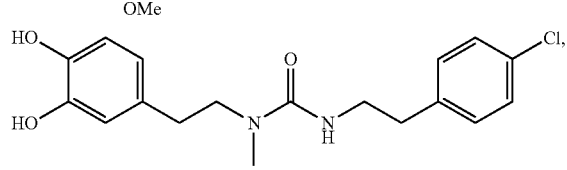
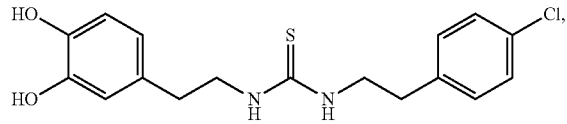
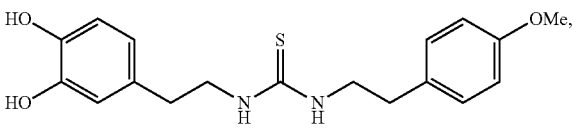
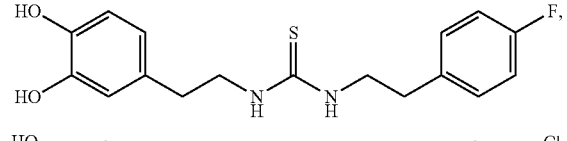
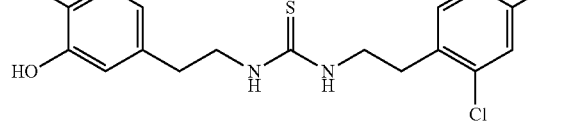
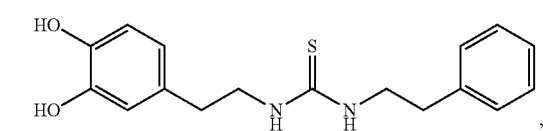
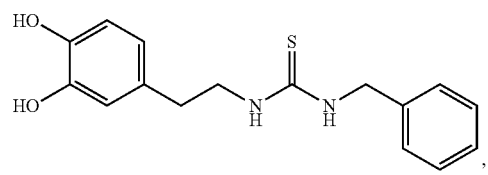

20
-continued

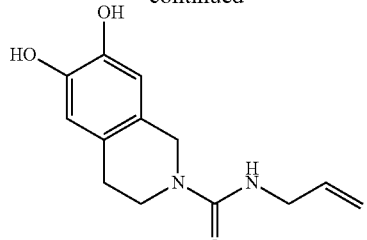
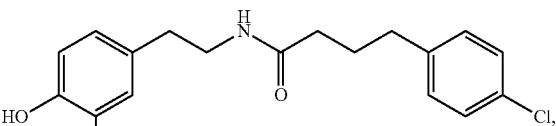
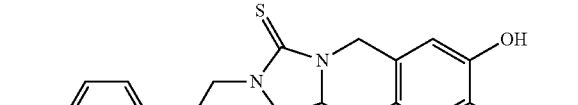
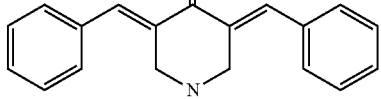
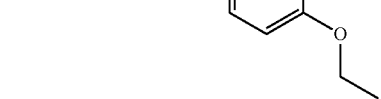

or a pharmaceutically acceptable salt or tautomer thereof.

In another aspect, the present disclosure provides a pharmaceutical composition comprising a compound of the present disclosure and a pharmaceutically acceptable excipient.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one of these drawings in combination with the detailed description of specific embodiments presented herein.

DESCRIPTION OF ILLUSTRATIVE EMBODIMENTS

Figure 1:
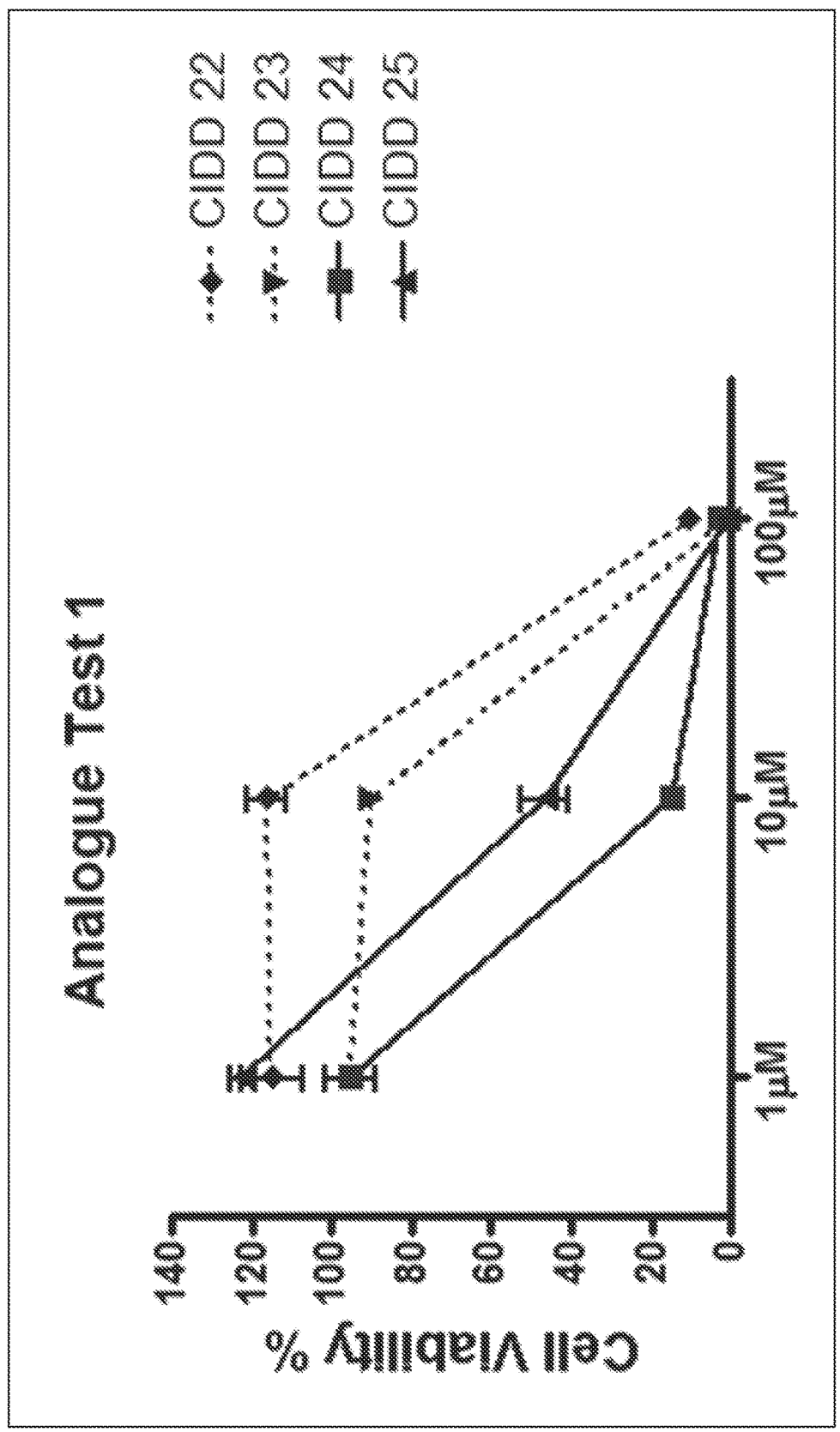
FIG. 1—Graph of cell viability as a function of concentration of novel analogs of capsazepine.

In some aspects of the present disclosure, the disclosure provides capsazepine derivatives which may be useful in the treatment of cancer. Such cancers that the compounds may be used to treating include but are not limited to breast, cervical, oral, head, neck, or prostate cancer. In some aspects, the compounds may be useful in treating a tumor by direct injection of the compound into the tumor, particularly an oral tumor. In other aspects, the compounds are administered systemically. The compounds of the present disclosure may also be used to treat the pain associated with a tumor for which it is being administered. In some embodiments, the compounds of the present disclosure are more therapeutically active or has at least one advantageous therapeutic property compared to capsazepine. These and other aspects of the disclosure are described in detail below.

I. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol ' ⁓⁓⁓ ' represents a single bond or a double bond. Thus, for example, the formula

includes

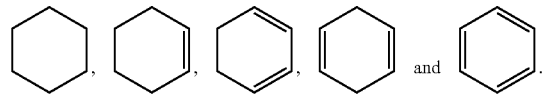

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol " ⁓⁓⁓ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol " ◂▨ " means a single bond where the group attached to the thick end of the wedge is "out of the page." The symbol " ◂▨ " means a single bond where the group attached to the thick end of the wedge is "into the page". The symbol " ⁓⁓⁓ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

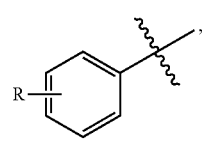

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

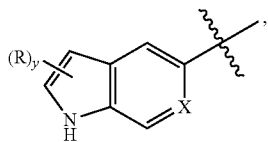

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. Also compare "phosphine$_{(C≤10)}$", which designates phosphine groups having from 0 to 10 carbon atoms. "Cn-n'" defines both the minimum (n) and maximum (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH; (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e., —F, —Cl, —Br, or —I) such that no other atoms aside from carbon, hydrogen and halogen are present. The group. —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

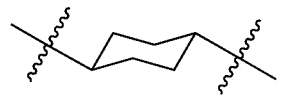 [SMILES: *C1CCC(*)CC1]

is a non-limiting example of cycloalkanediyl group. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkenyl" when used without the "substituted" modifier refers to an monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to an monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

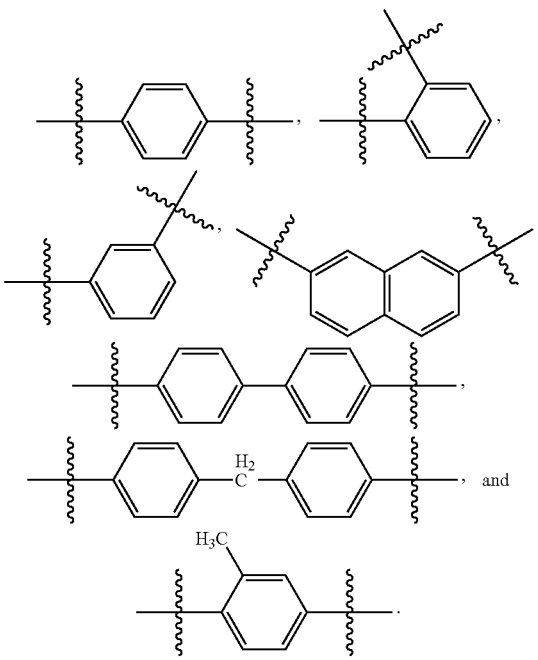

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH. —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —SH, —OCH$_3$, —OCH$_2$CH$_3$, —NHCH$_3$, —NHCH$_2$CH$_3$, —N(CH$_3$)$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$.

The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e., an enzyme, cell, cell receptor or microorganism) by half. In some embodiments, the IC$_{50}$ is a relative value compared to the conditions of the assay, experiment time, cells plated, or other reaction conditions.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, horse, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

II. COMPOUNDS OF THE PRESENT DISCLOSURE

In the present disclosure, attempts to synthesize novel anticancer agents of capsazepine are described. The novel capsazepine derivatives described in this disclosure can be prepared according to the methods described in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein. In some embodiments, the present disclosure contains a compound of the formula as described in Table 1.

TABLE 1

Compounds of the Present Disclosure

| Identification Number | Structure | IUPAC Name |
|---|---|---|
| CIDD-0000022 | 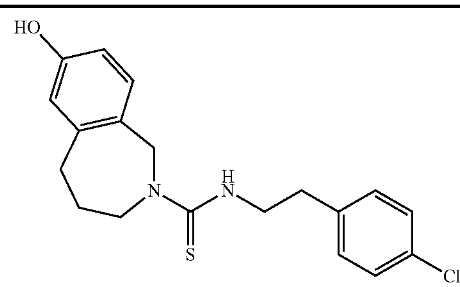 | N-[2-(4-chlorophenyl)ethyl]-7-hydroxy-2,3,4,5-tetrahydro-1H-2-benzazepine-2-carbothioamide |
| CIDD-0000023 | 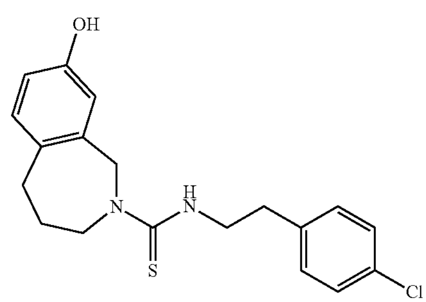 [SMILES: Oc1ccc2c(c1)CN(C(=S)NCCc1ccc(Cl)cc1)CCC2] | N-[2-(4-chlorophenyl)ethyl]-8-hydroxy-2,3,4,5-tetrahydro-1H-2-benzazepine-2-carbothioamide |
| CIDD-0000024 | 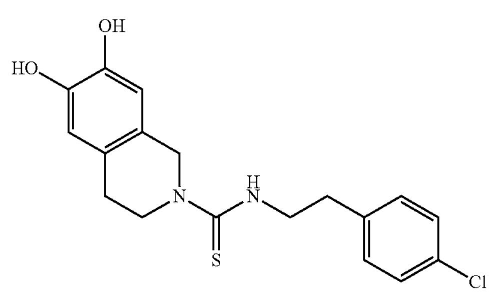 [SMILES: Oc1cc2c(cc1O)CN(C(=S)NCCc1ccc(Cl)cc1)CC2] | N-[2-(4-chlorophenyl)ethyl]-6,7-dihydroxy-1,2,3,4-tetrahydroisoquinoline-2-carbothioamide |

TABLE 1-continued

Compounds of the Present Disclosure

| Identification Number | Structure | IUPAC Name |
|---|---|---|
| CIDD-0000025 | 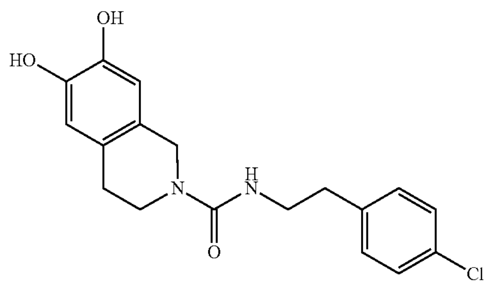 [SMILES: O=C(NCCc1ccc(Cl)cc1)N1CCc2cc(O)c(O)cc2C1] | N-[2-(4-chlorophenyl)ethyl]-6,7-dihydroxy-1,2,3,4-tetrahydroisoquinoline-2-carboxamide |
| CIDD-0000026 | 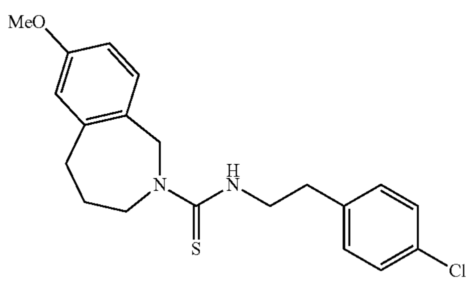 [SMILES: COc1ccc2c(c1)CCCN(C(=S)NCCc1ccc(Cl)cc1)C2] | N-[2-(4-chlorophenyl)ethyl]-7-methoxy-2,3,4,5-tetrahydro-1H-2-benzazepine-2-carbothioamide |
| CIDD-0000027 | 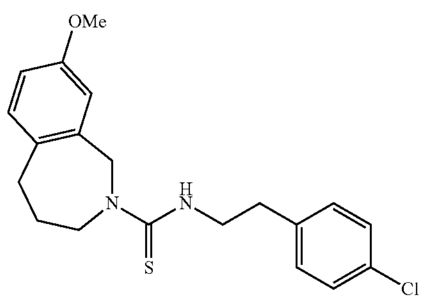 [SMILES: COc1ccc2c(c1)CN(C(=S)NCCc1ccc(Cl)cc1)CCC2] | N-[2-(4-chlorophenyl)ethyl]-8-methoxy-2,3,4,5-tetrahydro-1H-2-berizazepine-2-carbothioamide |
| CIDD-0000028 | 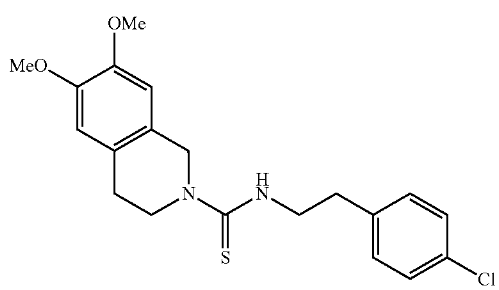 [SMILES: COc1cc2c(cc1OC)CN(C(=S)NCCc1ccc(Cl)cc1)CC2] | N-[2-(4-chlorophenyl)ethyl]-6,7-dimethoxy-1,2,3,4-tetrahydroisoquinoline-2-carbothioamide |
| CIDD-0000029 | 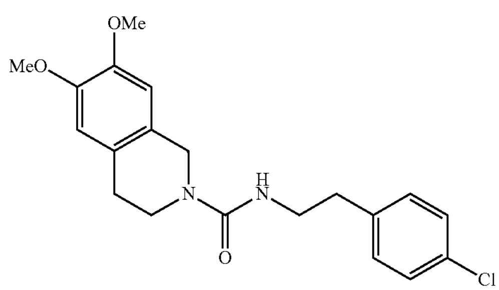 [SMILES: COc1cc2c(cc1OC)CN(C(=O)NCCc1ccc(Cl)cc1)CC2] | N-[2-(4-chlorophenyl)ethyl]-6,7-dimethoxy-1,2,3,4-tetrahydroisoquinoline-2-carboxamide |

TABLE 1-continued

Compounds of the Present Disclosure

| Identification Number | Structure | IUPAC Name |
|---|---|---|
| CIDD-0000030 | 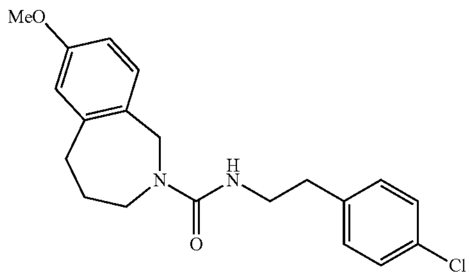 [SMILES: COc1ccc2c(c1)CCCN(C(=O)NCCc1ccc(Cl)cc1)C2] | N-[2-(4-chlorophenyl)ethyl]-7-methoxy-2,3,4,5-tetrahydro-1H-2-benzazepine-2-carboxamide |
| CIDD-0000031 | 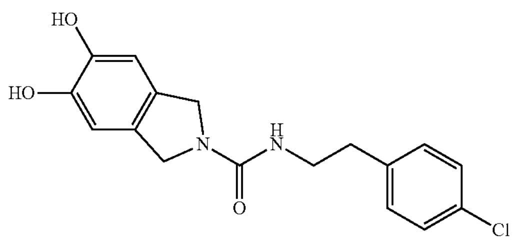 [SMILES: O=C(NCCc1ccc(Cl)cc1)N1Cc2cc(O)c(O)cc2C1] | N-[2-(4-chlorophenyl)ethyl]-5,6-dihydroxy-2,3-dihydro-1H-isoindole-2-carbothioamide |
| CIDD-0000032 | 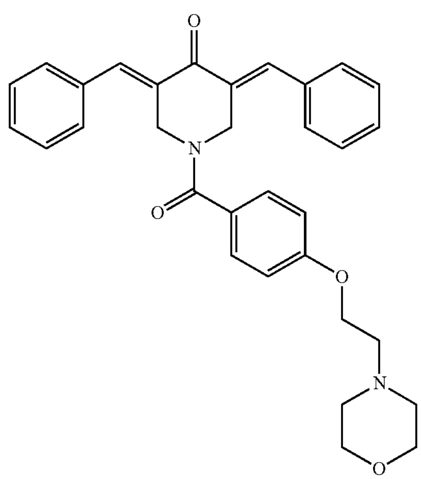 [SMILES: O=C1/C(=C/c2ccccc2)CN(C(=O)c2ccc(OCCN3CCOCC3)cc2)C/C1=C\c1ccccc1] | (3E,5E)-1-{4-[2-(morpholin-4-yl)ethoxy]benzoyl}-3,5-bis(phenylmethylidene)piperidin-4-one |
| CIDD-0000036 | 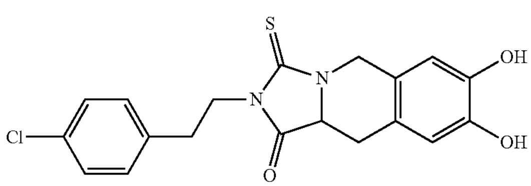 [SMILES: O=C1C2Cc3cc(O)c(O)cc3CN2C(=S)N1CCc1ccc(Cl)cc1] | 2-[2-(4-chlorophenyl)ethyl]-7,8-dihydroxy-3-sulfanylidene-1H,2H,3H,5H,10H,10aH-imidazolidino[1,5-b]isoquinolin-1-one |
| CIDD-0000037 | 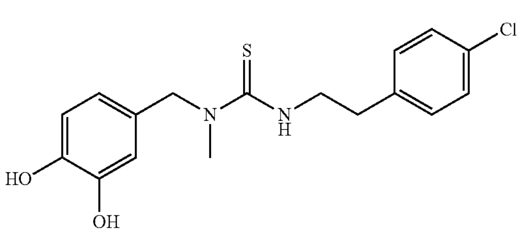 [SMILES: CN(Cc1ccc(O)c(O)c1)C(=S)NCCc1ccc(Cl)cc1] | 1-[2-(4-chlorophenyl)ethyl]-3-[(3,4-dihydroxyphenyl)methyl]-3-methylthiourea |

TABLE 1-continued

Compounds of the Present Disclosure

| Identification Number | Structure | IUPAC Name |
|---|---|---|
| CIDD-0000056 | 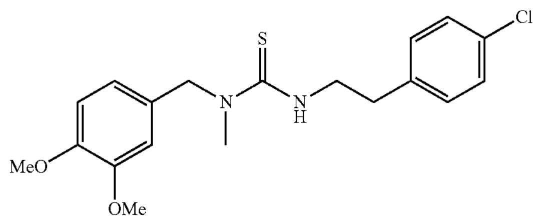 [SMILES: COc1ccc(CN(C)C(=S)NCCc2ccc(Cl)cc2)cc1OC] | 1-[2-(4-chlorophenyl)ethyl]-3-[(3,4-dimethoxyphenyl)methyl]-3-methylthiourea |
| CIDD-0000057 | 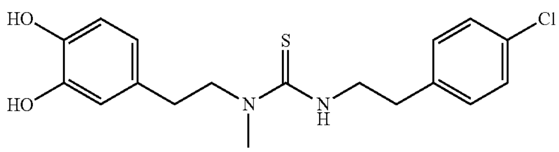 [SMILES: CN(CCc1ccc(O)c(O)c1)C(=S)NCCc1ccc(Cl)cc1] | 1-[2-(4-chlorophenyl)ethyl]-3-[2-(3,4-dihydroxyphenyl)ethyl]-3-methylthiourea |
| CIDD-0000058 | 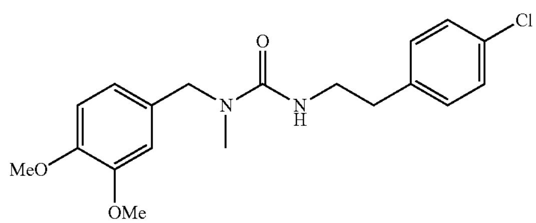 [SMILES: COc1ccc(CN(C)C(=O)NCCc2ccc(Cl)cc2)cc1OC] | 1-[2-(4-chlorophenyl)ethyl]-3-[(3,4-dimethoxyphenyl)methyl]-3-methylurea |
| CIDD-0000059 | 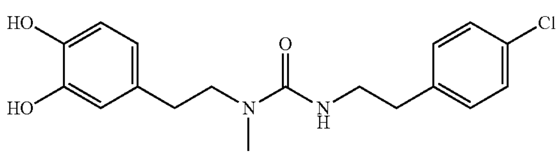 [SMILES: CN(CCc1ccc(O)c(O)c1)C(=O)NCCc1ccc(Cl)cc1] | 1-[2-(4-chlorophenyl)ethyl]-3-[2-(3,4-dihydroxyphenyl)ethyl]-3-methylurea |
| CIDD-0000060 | 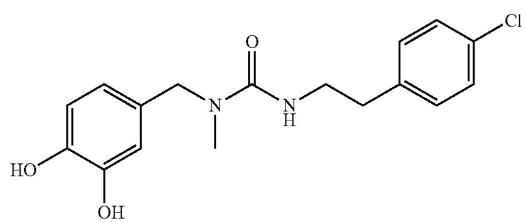 | 1-[2-(4-chlorophenyl)ethyl]-3-[(3,4-dihydroxyphenyl)methyl]-3-methylurea |
| CIDD-0000093 | 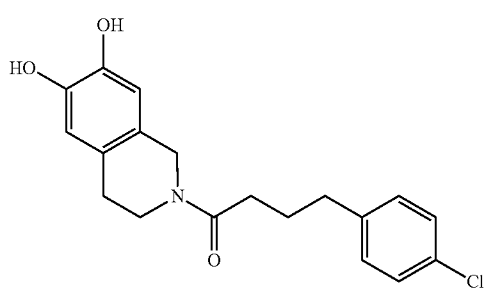 [SMILES: O=C(CCCc1ccc(Cl)cc1)N1CCc2cc(O)c(O)cc2C1] | 4-(4-chlorophenyl)-1-(6,7-dihydroxy-1,2,3,4-tetrahydroisoquinolin-2-yl)butan-1-one |
| CIDD-0000094 | 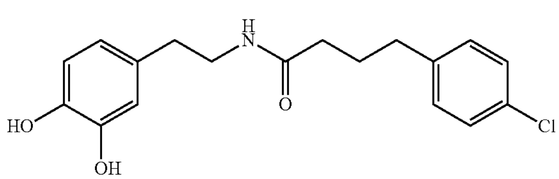 [SMILES: O=C(CCCc1ccc(Cl)cc1)NCCc1ccc(O)c(O)c1] | 4-(4-chlorophenyl)-N-[2-(3,4-dihydroxyphenyl)ethyl]butanamide |

TABLE 1-continued

Compounds of the Present Disclosure

| Identification Number | Structure | IUPAC Name |
|---|---|---|
| CIDD-0000097 | 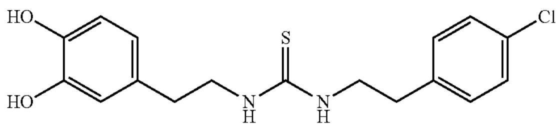 [SMILES: Oc1ccc(CCNC(=S)NCCc2ccc(Cl)cc2)cc1O] | 1-[2-(4-chlorophenyl)ethyl]-3-[2-(3,4-dihydroxyphenyl)ethyl]thiourea |
| CIDD-0000098 | 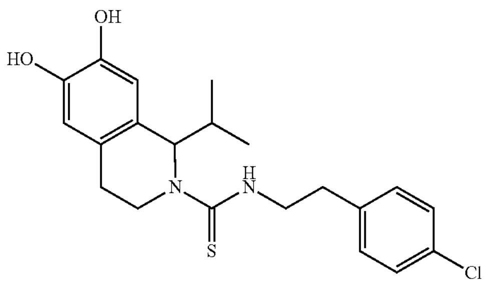 [SMILES: CC(C)C1c2cc(O)c(O)cc2CCN1C(=S)NCCc1ccc(Cl)cc1] | N-[2-(4-chlorophenyl)ethyl]-6,7-dihydroxy-1-(propan-2-yl)-1,2,3,4-tetrahydroisoquinoline-2-carbothioamide |
| CIDD-0000099 | 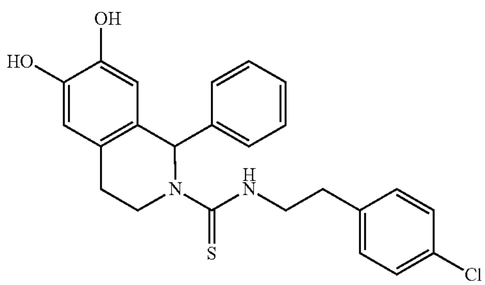 [SMILES: Oc1cc2c(cc1O)C(c1ccccc1)N(C(=S)NCCc1ccc(Cl)cc1)CC2] | N-[2-(4-chlorophenyl)ethyl]-6,7-dihydroxy-1-phenyl-1,2,3,4-tetrahydroisoquinoline-2-carbothioamide |
| CIDD-0000100 | 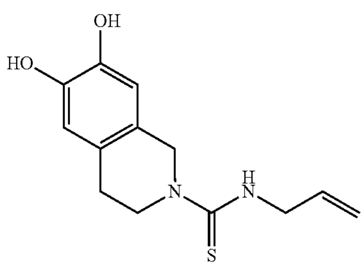 [SMILES: C=CCNC(=S)N1CCc2cc(O)c(O)cc2C1] | 6,7-dihydroxy-N-(prop-2-en-1-yl)-1,2,3,4-tetrahydroisoquinoline-2-carbothioamide |
| CIDD-0000103 | 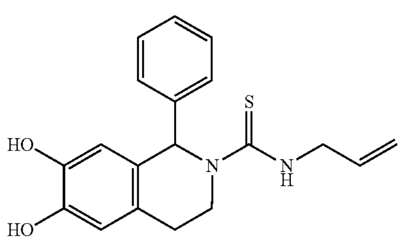 [SMILES: C=CCNC(=S)N1CCc2cc(O)c(O)cc2C1c1ccccc1] | 6,7-dihydroxy-1-phenyl-N-(prop-2-en-1-yl)-1,2,3,4-tetrahydroisoquinoline-2-carbothioamide |
| CIDD-0000104 | 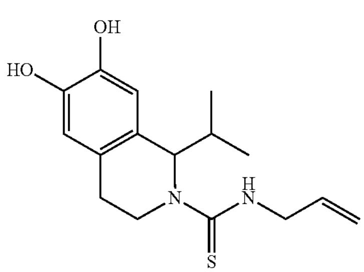 [SMILES: C=CCNC(=S)N1CCc2cc(O)c(O)cc2C1C(C)C] | 6,7-dihydroxy-N-(prop-2-en-1-yl)-1-(propan-2-yl)-1,2,3,4-tetrahydroisoquinoline-2-carbothioamide |

TABLE 1-continued

Compounds of the Present Disclosure

| Identification Number | Structure | IUPAC Name |
|---|---|---|
| CIDD-0000105 | 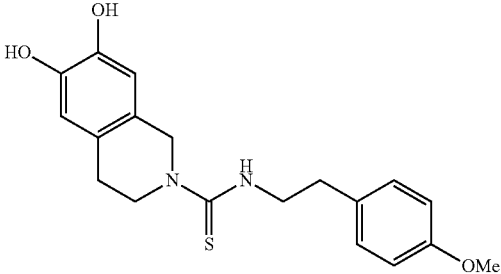 | 6,7-dihydroxy-N-[2-(4-methoxyphenyl)ethyl]-1,2,3,4-tetrahydroisoquinoline-2-carbothioamide |
| CIDD-0000106 | 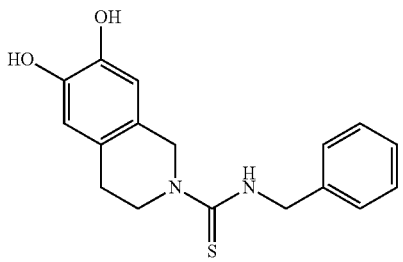 | N-benzyl-6,7-dihydroxy-1,2,3,4-tetrahydroisoquinoline-2-carbothioamide |
| CIDD-0000107 | 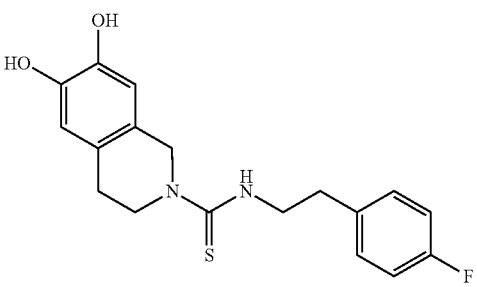 | N-[2-(4-fluorophenyl)ethyl]-6,7-dihydroxy-1,2,3,4-tetrahydroisoquinoline-2-carbothioamide |
| CIDD-0000108 | 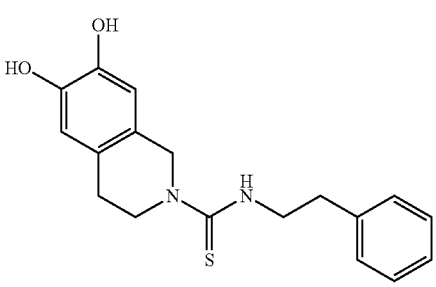 | 6,7-dihydroxy-N-(2-phenylethyl)-1,2,3,4-tetrahydroisoquinoline-2-carbothioamide |
| CIDD-0000109 | 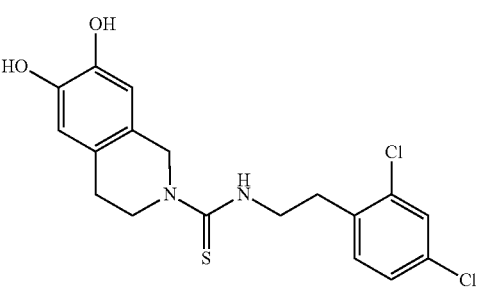 [SMILES: Oc1cc2c(cc1O)CN(C(=S)NCCc1ccc(Cl)cc1Cl)CC2] | N-[2-(2,4-dichlorophenyl)ethyl]-6,7-dihydroxy-1,2,3,4-tetrahydroisoquinoline-2-carbothioamide |
| CIDD-0000110 | 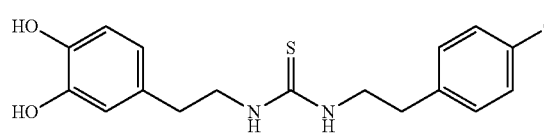 | 1-[2-(3,4-dihydroxyphenyl)ethyl]-3-[2-(4-methoxyphenyl)ethyl]thiourea |

TABLE 1-continued

Compounds of the Present Disclosure

| Identification Number | Structure | IUPAC Name |
|---|---|---|
| CIDD-0000111 | 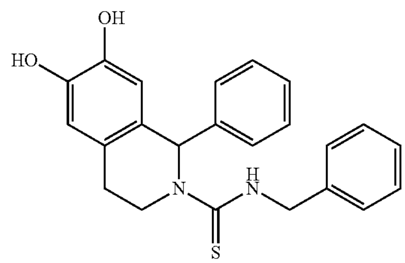 [SMILES: Oc1cc2c(cc1O)C(c1ccccc1)N(C(=S)NCc1ccccc1)CC2] | N-benzyl-6,7-dihydroxy-1-phenyl-1,2,3,4-tetrahydroisoquinoline-2-carbothioamide |
| CIDD-0000112 | 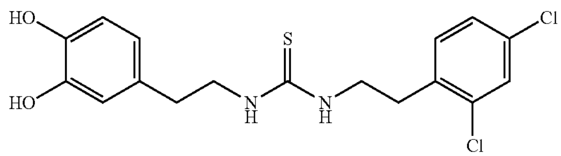 [SMILES: Oc1ccc(CCNC(=S)NCCc2ccc(Cl)cc2Cl)cc1O] | 1-[2-(2,4-dichlorophenyl)ethyl]-3-[2-(3,4-dihydroxyphenyl)ethyl]thiourea |
| CIDD-0000113 | 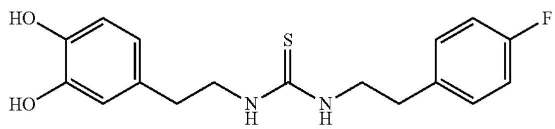 [SMILES: Oc1ccc(CCNC(=S)NCCc2ccc(F)cc2)cc1O] | 3-[2-(3,4-dihydroxyphenyl)ethyl]-1-[2-(4-fluorophenyl)ethyl]thiourea |
| CIDD-0000114 | 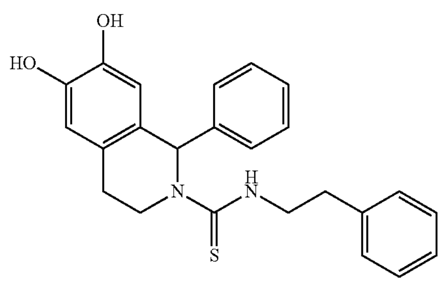 [SMILES: Oc1cc2c(cc1O)C(c1ccccc1)N(C(=S)NCCc1ccccc1)CC2] | 6,7-dihydroxy-1-phenyl-N-(2-phenylethyl)-1,2,3,4-tetrahydroisoquinoline-2-carbothioamide |
| CIDD-0000115 | 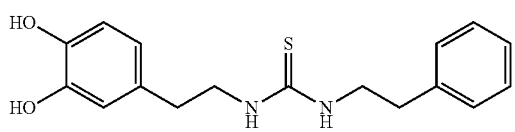 [SMILES: Oc1ccc(CCNC(=S)NCCc2ccccc2)cc1O] | 3-[2-(3,4-dihydroxyphenyl)ethyl]-1-(2-phenylethyl)thiourea |
| CIDD-0000116 | 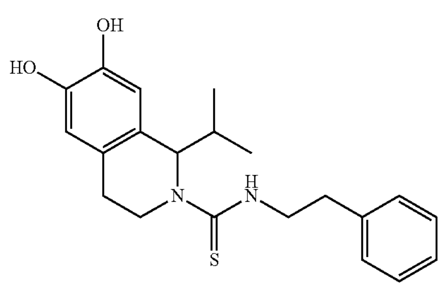 [SMILES: CC(C)C1c2cc(O)c(O)cc2CCN1C(=S)NCCc1ccccc1] | 6,7-dihydroxy-N-(2-phenylethyl)-1-(propan-2-yl)-1,2,3,4-tetrahydroisoquinoline-2-carbothioamide |
| CIDD-0000117 | 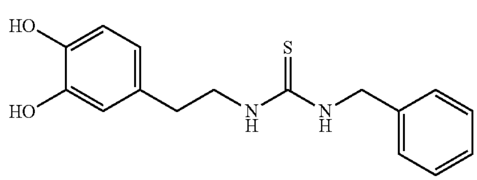 [SMILES: Oc1ccc(CCNC(=S)NCc2ccccc2)cc1O] | 1-benzyl-3-[2-(3,4-dihydroxyphenyl)ethyl]thiourea |

TABLE 1-continued

Compounds of the Present Disclosure

| Identification Number | Structure | IUPAC Name |
|---|---|---|
| CIDD-0000118 | 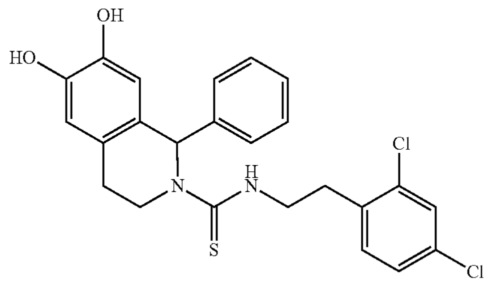 [SMILES: Oc1cc2c(cc1O)C(c1ccccc1)N(C(=S)NCCc1ccc(Cl)cc1Cl)CC2] | N-[2-(2,4-dichlorophenyl)ethyl]-6,7-dihydroxy-1-phenyl-1,2,3,4-tetrahydroisoquinoline-2-carbothioamide |
| CIDD-0000123 | 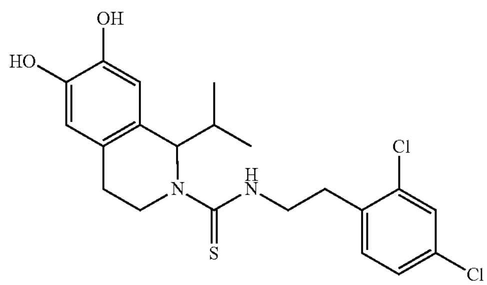 [SMILES: CC(C)C1c2cc(O)c(O)cc2CCN1C(=S)NCCc1ccc(Cl)cc1Cl] | N-[2-(2,4-dichlorophenyl)ethyl]-6,7-dihydroxy-1-(propan-2-yl)-1,2,3,4-tetrahydroisoquinoline-2-carbothioamide |
| CIDD-0000128 | 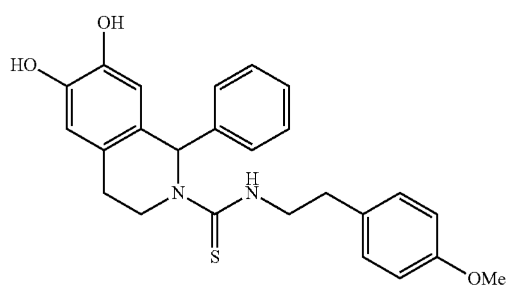 [SMILES: COc1ccc(CCNC(=S)N2CCc3cc(O)c(O)cc3C2c2ccccc2)cc1] | 6,7-dihydroxy-N-[2-(4-methoxyphenyl)ethyl]-1-phenyl-1,2,3,4-tetrahydroisoquinoline-2-carbothioamide |
| CIDD-0000129 | 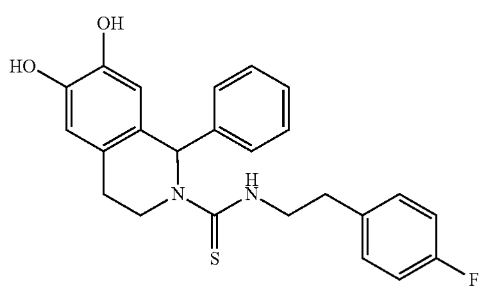 [SMILES: Oc1cc2c(cc1O)C(c1ccccc1)N(C(=S)NCCc1ccc(F)cc1)CC2] | N-[2-(4-fluorophenyl)ethyl]-6,7-dihydroxy-1-phenyl-1,2,3,4-tetrahydroisoquinoline-2-carbothioamide |
| CIDD-0000132 | 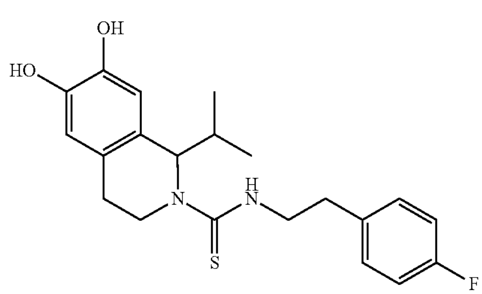 [SMILES: CC(C)C1c2cc(O)c(O)cc2CCN1C(=S)NCCc1ccc(F)cc1] | N-[2-(4-fluorophenyl)ethyl]-6,7-dihydroxy-1-(propan-2-yl)-1,2,3,4-tetrahydroisoquinoline-2-carbothioamide |

TABLE 1-continued

Compounds of the Present Disclosure

| Identification Number | Structure | IUPAC Name |
|---|---|---|
| CIDD-0000133 | 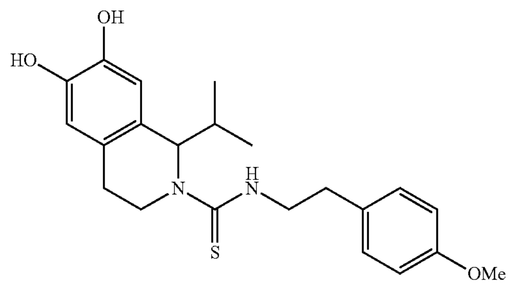 [SMILES: COc1ccc(CCNC(=S)N2CCc3cc(O)c(O)cc3C2C(C)C)cc1] | 6,7-dihydroxy-N-[2-(4-methoxyphenyl)ethyl]-1-(propan-2-yl)-1,2,3,4-tetrahydroisoquinoline-2-carbothioamide |
| CIDD-0000134 | 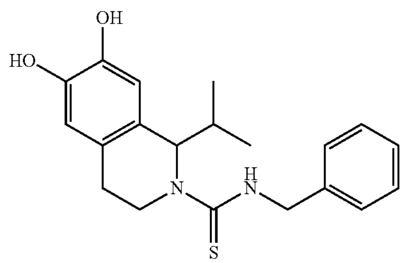 [SMILES: CC(C)C1c2cc(O)c(O)cc2CCN1C(=S)NCc1ccccc1] | N-benzyl-6,7-dihydroxy-1-(propan-2-yl)-1,2,3,4-tetrahydroisoquinoline-2-carbothioamide |
| CIDD-0052319 | 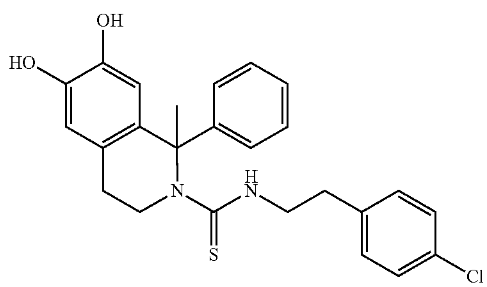 | N-[2-(4-chlorophenyl)ethyl]-6,7-dihydroxy-1-methyl-1-phenyl-1,2,3,4-tetrahydroisoquinoline-2-carbothioamide |

The novel capsazepine derivatives described in this disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The novel capsazepine derivatives may occur as racemates and racemic mixtures, single enantiomers, diastereomeric mixtures and individual diastereomers. In some embodiments, a single diastereomer is obtained. The chiral centers of the present disclosure can have the S or the R configuration.

In addition, atoms making up the novel capsazepine derivatives of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of the novel capsazepine derivatives may be replaced by a sulfur or selenium atom(s).

The novel capsazepine derivatives may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical advantages over, compounds known in the prior art for use in the indications stated herein.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

III. HYPERPROLIFERATIVE DISEASES

While hyperproliferative diseases can be associated with any disease which causes a cell to begin to reproduce uncontrollably, cancer is the common example. One of the key elements of cancer is that the cell's normal apoptotic cycle is interrupted and thus agents that lead to apoptosis of the cell are important therapeutic agents for treating these diseases. In this disclosure, the novel capsazepine derivatives have been shown to lead to cellular apoptosis and as such can potentially be used to treat a variety of types of cancer lines. As such, the novel capsazepine derivatives may be used to effectively treat cancers such as an oral tumor, a tumor of the head or neck, breast cancer, cervical cancer, or prostate cancer. In various aspects, it is anticipated that compounds of the present disclosure may be used to treat virtually any malignancy.

Cancer cells that may be treated with the capsazepine derivatives of the present disclosure according to the embodiments include but are not limited to cells from the bladder, blood, bone, bone marrow, brain, breast, colon, esophagus, gastrointestine, gum, head, kidney, liver, lung, nasopharynx, neck, oral, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor, nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

IV. PHARMACEUTICAL FORMULATIONS AND ROUTES OF ADMINISTRATION

For administration to a mammal in need of such treatment, the novel capsazepine derivatives in a therapeutically effective amount are ordinarily combined with one or more excipients appropriate to the indicated route of administration. The novel capsazepine derivatives may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the novel capsazepine derivatives may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present disclosure may be subjected to conventional pharmaceutical operations such as sterilization and/or may contain conventional pharmaceutical carriers and excipients such as preservatives, stabilizers, wetting agents, emulsifiers, buffers, etc.

The novel capsazepine derivatives may be administered by a variety of methods, e.g., orally or by injection (e.g., subcutaneous, intratumoral, intravenous, intraperitoneal, etc.). Depending on the route of administration, the novel capsazepine derivatives may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the novel capsazepine derivatives with, or co-administer the novel capsazepine derivatives with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The novel capsazepine derivatives may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion are also envisioned. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the novel capsazepine derivatives in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The novel capsazepine derivatives can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the novel capsazepine derivatives may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the novel capsazepine derivatives in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of the novel capsazepine derivatives calculated to produce the desired therapeutic effect in association with the required pharmaceutical carrier. The specification for the dosage unit forms of the disclosure are dictated by and directly dependent on (a) the unique characteristics of the novel capsazepine derivatives described in this disclosure and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The novel capsazepine derivatives describe in this disclosure are administered at a therapeutically effective dosage sufficient to treat a condition associated with a condition in a patient. For example, the efficacy of the novel capsazepine derivatives can be evaluated in an animal model system that may be predictive of efficacy in treating the disease in humans, such as the model systems shown in the examples and drawings.

In some embodiments, the actual dosage amount of the novel capsazepine derivatives of the present disclosure or composition comprising the novel capsazepine derivatives of the present disclosure administered to a subject is determined by physical and physiological factors such as age, sex, body weight, severity of condition, the type of disease being treated, previous or concurrent therapeutic interventions, idiopathy of the subject and on the route of administration. These factors may be used by a skilled artisan to determine the appropriate dosage amount. The practitioner responsible for administration will typically determine the concentration of active ingredient(s) in a composition and appropriate dose(s) for the individual subject. The dosage may be adjusted by the individual physician in the event of any complication.

An effective amount typically will vary from about 2 mg/kg to about 50 mg/kg, in one or more dose administrations daily, for one or several days (depending of course of the mode of administration and the factors discussed above). In some particular embodiments, the amount is less than 5,000 mg per day with a range of 100 mg to 4500 mg per day.

In some embodiments, the effective amount is less than 10 mg/kg/day, less than 100 mg/kg/day, less than 250 mg/kg/day, less than 100 mg/kg/day, less than 50 mg/kg/day, less than 25 mg/kg/day or less than 10 mg/kg/day. Alternatively, in some embodiments, the range is 1 mg/kg/day to 200 mg/kg/day.

In other non-limiting examples, a dose may also comprise from about 10 mg/kg/body weight, about 100 mg/kg/body weight, about 10 g/kg/body weight, about 5 g/kg/body weight, or more per administration, and any range derivable therein. In non-limiting examples of a derivable range from the numbers listed herein, a range of about 1 mg/kg/body weight to about 100 mg/kg/body weight, about 5 g/kg/body weight to about 10 g/kg/body weight, etc., can be administered, based on the numbers described above.

In certain embodiments, a pharmaceutical composition of the present disclosure may comprise, for example, at least about 0.1% of a novel capsazepine derivative described in the present disclosure. In other embodiments, the compound of the present disclosure may comprise between about 0.25% to about 75% of the weight of the unit, or between about 25% to about 60%, or between about 1% to about 10%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The novel capsazepine derivatives may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the subject has eaten or will eat. In other embodiments, the disclosure is taken as a dietary supplement. In some embodiments, the novel capsazepine derivatives are taken before the onset of the tumor as a prophylaxis measure. In other embodiments, the novel capsazepine derivatives are taken as a treatment option for use as an antiproliferative agent.

V. COMBINATION THERAPY

In addition to being used as a monotherapy, the novel capsazepine derivatives described in the present disclosure may also find use in combination therapies. Effective combination therapy may be achieved with a single composition or pharmacological formulation that includes both agents, or with two distinct compositions or formulations, administered at the same time, wherein one composition includes a novel capsazepine derivative, and the other includes the second agent(s). The other therapeutic modality may be administered before, concurrently with, or following administration of the novel capsazepine derivatives. The therapy using the novel capsazepine derivatives may precede or follow administration of the other agent(s) by intervals ranging from minutes to weeks. In embodiments where the other agent and the novel capsazepine derivatives are administered separately, one would generally ensure that a significant period of time did not expire between the time of each delivery, such that each agent would still be able to exert an advantageously combined effect. In such instances, it is contemplated that one would typically administer the novel capsazepine derivatives and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of a novel capsazepine derivative, or the other agent will be desired. In this regard, various combinations may be employed. By way of illustration, where the novel capsazepine derivatives is "A" and the other agent is "B", the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated. Non-limiting examples of pharmacological agents that may be used in the present disclosure include any pharmacological agent known to be of benefit in the treatment of a cancer or hyperproliferative disorder or disease. In some embodiments, combinations of the novel capsazepine derivatives with a cancer targeting immunotherapy, radiotherapy, chemotherapy, or surgery are contemplated. Also contemplated is a combination of a novel capsazepine derivative with more than one of the above mentioned methods including more than one type of a specific therapy. In some embodiments, it is contemplated that the immunotherapy is a monoclonal antibody which targets HER2/neu such trastuzumab (Herceptin®) or a similar antibody. In other embodiments, the immunotherapy can be other cancer targeting antibodies such as alemtuzumab (Campath®), bevacizumab (Avastin®), cetuximab (Erbitux®), and panitumumab (Vectibix®) or conjugated antibodies such as ibritumomab tiuxetan (Zevalin®), tositumomab (Bexxar®), brentuximab vedotin (Adcetris®), ado-trastuzumab emtansine (Kadcyla™), or denileukin dititox (Ontak®) as well as immune cell targeting antibodies such as ipilimumab (Yervoy®), tremelimumab, anti-PD-1, anti-4-1-BB, anti-GITR, anti-TIM3, anti-LAG-3, anti-TIGIT, anti-CTLA-4, or anti-LIGHT. Additionally, in some embodiments, the novel capsazepin derivatives can be administered with gefitinib, TAE684, tivantinib, or combinations of these drugs. Furthermore, in some embodiments, the novel capsazepine derivatives are envisioned to be used in combination therapies with dendritic cell-based immunotherapies such as Sipuleucel-T (Provenge®) or adoptive T-cell immunotherapies.

Furthermore, it is contemplated that the novel capsazepine derivatives are used in combination with a chemotherapeutic agent such as gefitinib, TAE684, tivantinib, anthracyclines, taxanes, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, oxaliplatin, BRAF inhibitors, and TGF-beta inhibitors. In some embodiments, the combination therapy is designed to target a cancer such as those listed above. In the preferred embodiments, the cancer the combination therapy is designed to treat is a cancer of the neck, mouth, or head, breast cancer, lung cancer, prostate cancer, cervical cancer, or other epithelial derived solid tumors.

1. Chemotherapy

In some embodiments, the capsazepine derivatives of the present disclosure can be used in conjunction with one or more additional chemotherapies. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); 47inblast; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

In some embodiments, the capsazepine derivatives of the present disclosure can be used in conjunction with radiotherapy. Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Without being bound by theory, radiotherapy can increase the amount of reactive oxygen species in tumor cells. In some embodiments, the combination therapy of the compounds of the present disclosure and radiotherapy can enhance the production of reactive oxygen species and thus the anti-tumor effects of the treatment. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In some embodiments, the capsazepine derivatives of the present disclosure can be used in conjunction with one or more additional immunotherapies. In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-6, IL-10, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

In some embodiments, the capsazepine derivatives of the present disclosure can be used in conjunction with surgery. Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present disclosure to improve the anti-hyperproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15 Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results

1. Synthesis of Analogs of Capsazepine

Compounds of Formula I, or their pharmaceutically acceptable salts, can be prepared according to the reaction schemes described herein. Unless otherwise noted, the formula is as defined above and in the claims that follow.

Treatment of an amine of 1 with an appropriately substituted aldehyde or ketone, in the presence of trifluoroacetic acid in dichloromethane, at temperatures ranging from room temperature to 150° C., produces the desired cyclized compound 2. Alternative conditions for this transformation also include the use of microwave irradiation. Other suitable conditions for this transformation include the use of Lewis acids such as titanium tetraisopropoxide, titanium tetrachloride, boron trifluoride etherate and related Lewis acids. Treatment of compound 2 with an appropriately substitute isocyanate or thioisocyanate in the presence of a tertiary amine base, such as triethylamine and dichloromethane, at temperatures ranging from room temperature to 80° C., produces the desired urea (X=O) or thiourea (X=S) compounds 3. The appropriately substitute isocyanate or thioisocyanate reagents can be prepared from the corresponding amines and thiocarbonyl diimidazole.

Scheme 1: Synthesis of Urea or Thiourea Compounds

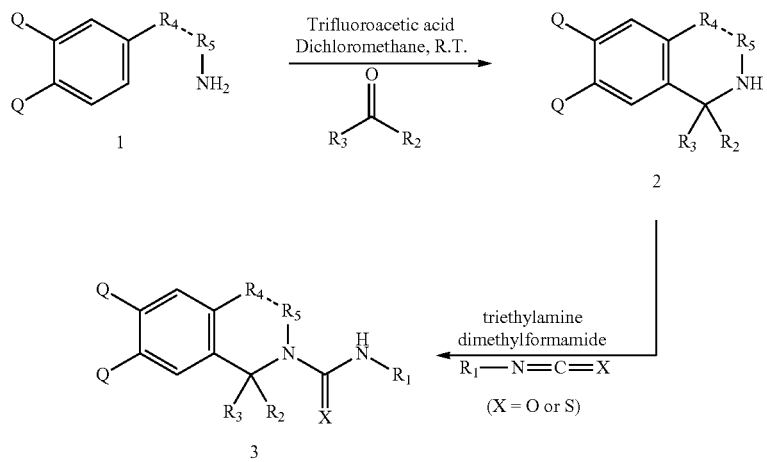

wherein Q is hydrogen, hydroxy, halo, alkyl$_{(C≤12)}$, substituted alkyl$_{(C≤12)}$, alkoxy$_{(C≤12)}$, or substituted alkoxy$_{(C≤12)}$; X is O or S; $R_1$ is alkenyl$_{(C≤12)}$, aryl$_{(C≤12)}$, aralkyl$_{(C≤12)}$, or a substituted version of any of these groups; $R_2$ and $R_3$ are each independently hydrogen, alkyl$_{(C≤12)}$, substituted alkyl$_{(C≤12)}$, aryl$_{(C≤12)}$, or substituted aryl$_{(C≤12)}$; $R_4$ and $R_5$ are each independently hydrogen, a covalent bond, alkanediyl$_{(C≤6)}$, or substituted alkanediyl$_{(C≤6)}$;

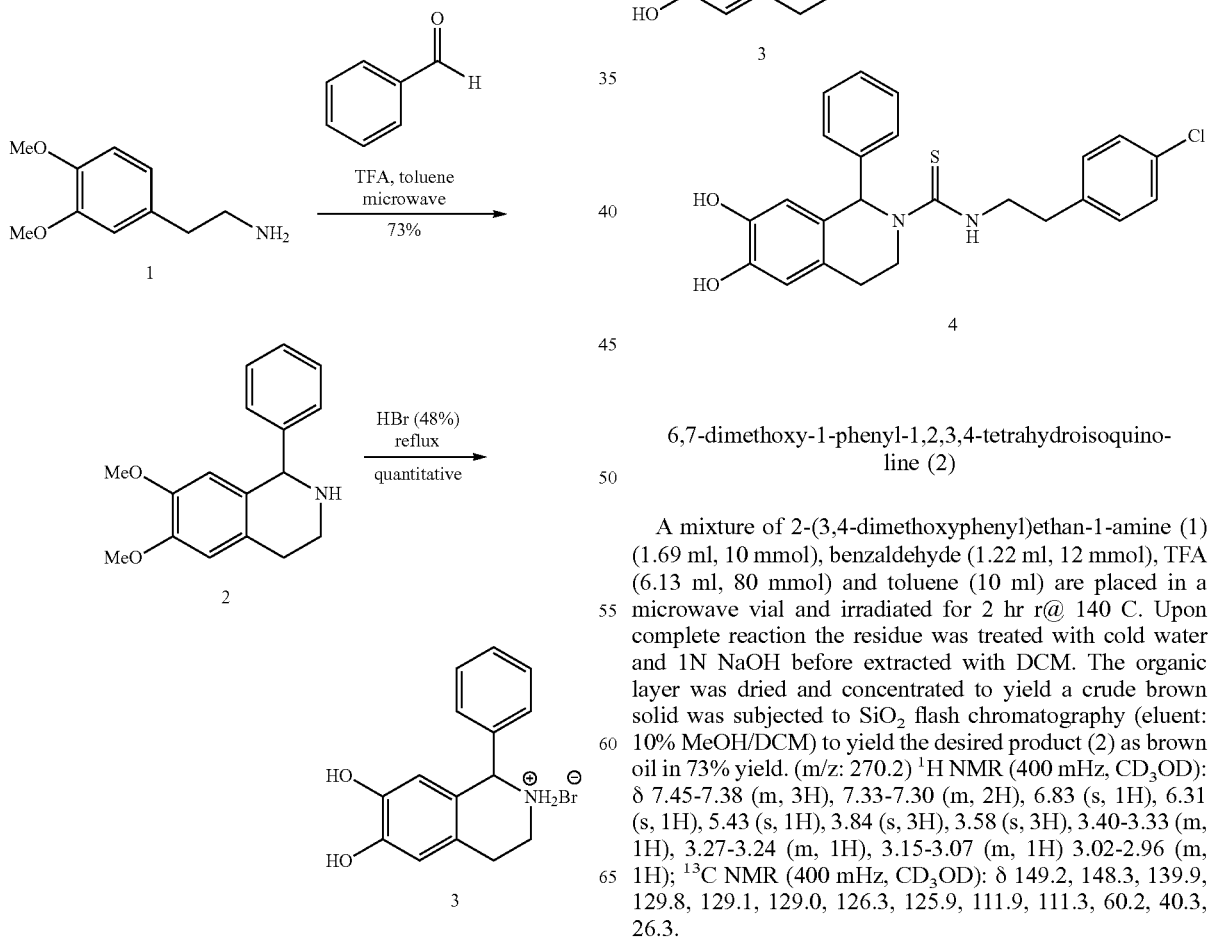

6,7-dimethoxy-1-phenyl-1,2,3,4-tetrahydroisoquinoline (2)

A mixture of 2-(3,4-dimethoxyphenyl)ethan-1-amine (1) (1.69 ml, 10 mmol), benzaldehyde (1.22 ml, 12 mmol), TFA (6.13 ml, 80 mmol) and toluene (10 ml) are placed in a microwave vial and irradiated for 2 hr r@ 140 C. Upon complete reaction the residue was treated with cold water and 1N NaOH before extracted with DCM. The organic layer was dried and concentrated to yield a crude brown solid was subjected to SiO$_2$ flash chromatography (eluent: 10% MeOH/DCM) to yield the desired product (2) as brown oil in 73% yield. (m/z: 270.2) $^1$H NMR (400 mHz, CD$_3$OD): δ 7.45-7.38 (m, 3H), 7.33-7.30 (m, 2H), 6.83 (s, 1H), 6.31 (s, 1H), 5.43 (s, 1H), 3.84 (s, 3H), 3.58 (s, 3H), 3.40-3.33 (m, 1H), 3.27-3.24 (m, 1H), 3.15-3.07 (m, 1H) 3.02-2.96 (m, 1H); $^{13}$C NMR (400 mHz, CD$_3$OD): δ 149.2, 148.3, 139.9, 129.8, 129.1, 129.0, 126.3, 125.9, 111.9, 111.3, 60.2, 40.3, 26.3.

6,7-dihydroxy-1-phenyl-1,2,3,4-tetrahydroisoquinolin-2-ium bromide (3)

To a flask containing 6,7-dimethoxy-1-phenyl-1,2,3,4-tetrahydroisoquinoline (2) (500 mg, 1.8 mmol) was added HBr (48% in $H_2O$) (9 ml) and the reaction was stirred at reflux for 12 hrs. Upon full conversion to desired product, the solution was concentrated in vacuo to provide 6,7-dihydroxy-1-phenyl-1,2,3,4-tetrahydroisoquinolin-2-ium bromide (3) as a brown solid in quantitative yield. This material was used in subsequent reaction without further purification. (m/z: 242.2) $^1H$ NMR (400 mHz, $CD_3OD$): δ 7.50-7.48 (m, 3H), δ 7.47-7.38 (m, 2H), 6.70 (s, 1H), 6.20 (s, 1H), 5.60 (s, 1H), 3.52-3.44 (m, 2H), 3.19-3.04 (m, 1H) 3.02-3.00 (m, 1H); $^{13}C$ NMR (400 mHz, $CD_3OD$): δ 147.2, 145.9, 138.1, 130.9, 130.3, 124.4, 123.3, 116.0, 115.3, 61.0, 41.5, 25.6.

N-(4-chlorophenethyl)-6,7-dihydroxy-1-phenyl-3,4-dihydroisoquinoline-2 (1H)-carbothioamide (4)

To a stirring solution of 6,7-dihydroxy-1-phenyl-1,2,3,4-tetrahydroisoquinolin-2-ium bromide (3) (100 mg, 0.4 mmol) in DMF was added TEA (0.13 ml, 1.2 mmol) and the resulting solution stirred at room temperature for 15 min. To this, 2-(4-chlorophenethyl)isothiocyanate (0.078 ml, 0.48 mmol) was added and allowed to stir at room temperature for 1 hr. Upon complete reaction the solution was concentrated in vacuo. The remaining organic residue was diluted in EtOAc and washed several times with $H_2O$ and brine. The organic layer was concentrated in vacuo and the crude material was subjected to $SiO_2$ flash chromatography (eluent: 10% MeOH/DCM) to provide the desired product (4) in 26% yield. (m/z: 439.1) $^1HNMR$ (400 mHz, $CDCl_3$): δ 7.243-7.193 (m, 5H), δ 7.125-7.065 (m, 4H), 6.901 (br, 1H), 6.697 (s, 1H), 6.629 (s, 1H), 5.544 (t, J=5.4 Hz, 1H), 3.943 (q, J=5.6 Hz, 2H), 3.673 (br, 2H), 2.903 (td, J=Hz, 2H), 2.672-2.577 (m, 2H); $^{13}C$ NMR (400 mHz, $CDCl_3$): δ 181.3, 143.7, 142.2, 140.7, 137.3, 132.6, 130.3, 129.0, 128.7, 128.3, 127.6, 127.4, 126.9, 115.2, 114.8, 62.2, 47.0, 44.1, 34.7, 27.2.

TABLE 2

Compounds with Characterization Data

| Molecule Name | Structure | MW | Chemical formula | Observed MS m/z (m + 1) |
|---|---|---|---|---|
| CIDD-0000022 | 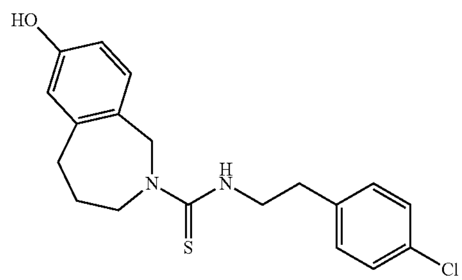 [SMILES: Oc1ccc2c(c1)CCCN(C(=S)NCCc1ccc(Cl)cc1)C2] | 360.901 | $C_{19}H_{21}ClN_2OS$ | 361.3 |
| CIDD-0000023 | 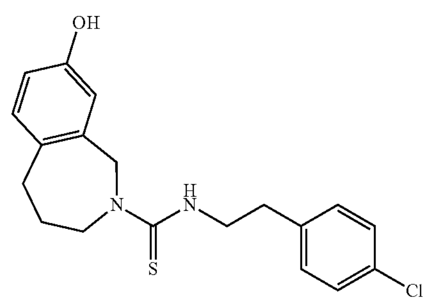 [SMILES: Oc1ccc2c(c1)CN(C(=S)NCCc1ccc(Cl)cc1)CCC2] | 360.901 | $C_{19}H_{21}ClN_2OS$ | 361.3 |
| CIDD-0000024 | 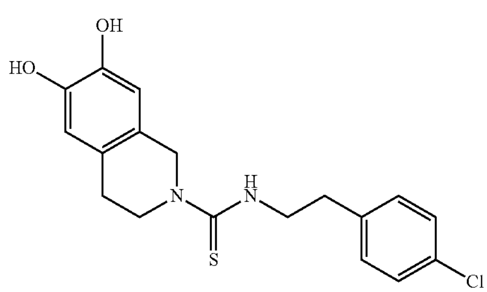 [SMILES: Oc1cc2c(cc1O)CN(C(=S)NCCc1ccc(Cl)cc1)CC2] | 362.874 | $C_{18}H_{19}ClN_2O_2S$ | 363.2 |

TABLE 2-continued

Compounds with Characterization Data

| Molecule Name | Structure | MW | Chemical formula | Observed MS m/z (m + 1) |
|---|---|---|---|---|
| CIDD-0000025 | 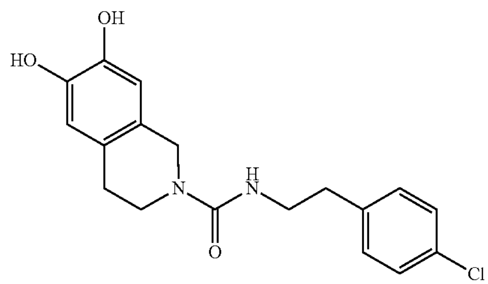 [SMILES: O=C(NCCc1ccc(Cl)cc1)N1CCc2cc(O)c(O)cc2C1] | 346.808 | $C_{18}H_{19}ClN_2O_3$ | 347.3 |
| CIDD-0000026 | 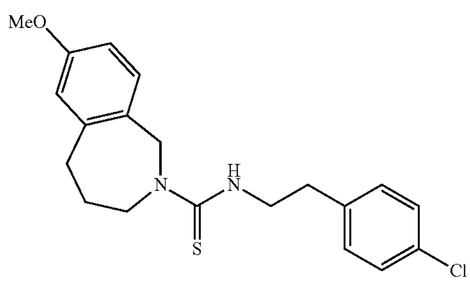 [SMILES: COc1ccc2c(c1)CCCN(C(=S)NCCc1ccc(Cl)cc1)C2] | 374.927 | $C_{20}H_{23}ClN_2OS$ | 375.3 |
| CIDD-0000027 | 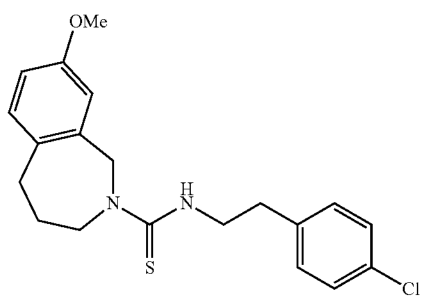 [SMILES: COc1ccc2c(c1)CN(C(=S)NCCc1ccc(Cl)cc1)CCC2] | 374.927 | $C_{20}H_{23}ClN_2OS$ | 375.3 |
| CIDD-0000028 | 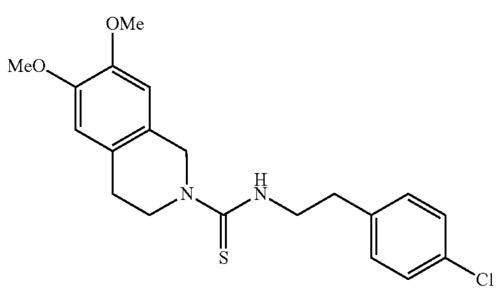 [SMILES: COc1cc2c(cc1OC)CN(C(=S)NCCc1ccc(Cl)cc1)CC2] | 390.927 | $C_{20}H_{23}ClN_2O_2S$ | 391.3 |
| CIDD-0000029 | 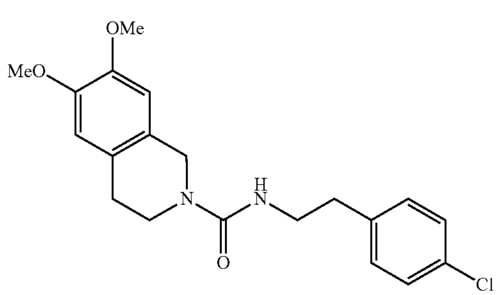 [SMILES: COc1cc2c(cc1OC)CN(C(=O)NCCc1ccc(Cl)cc1)CC2] | 374.861 | $C_{20}H_{23}ClN_2O_3$ | 375.3 |

TABLE 2-continued

Compounds with Characterization Data

| Molecule Name | Structure | MW | Chemical formula | Observed MS m/z (m + 1) |
|---|---|---|---|---|
| CIDD-0000030 | 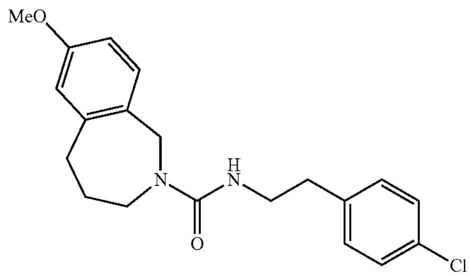 [SMILES: COc1ccc2c(c1)CCCN(C(=O)NCCc1ccc(Cl)cc1)C2] | 358.862 | $C_{20}H_{23}ClN_2O_2$ | 359.3 |
| CIDD-0000031 | 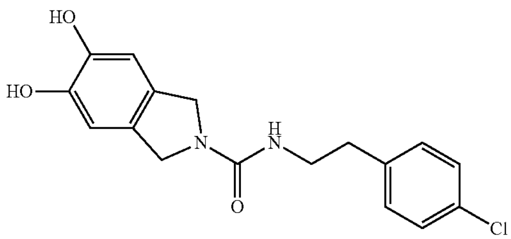 [SMILES: O=C(NCCc1ccc(Cl)cc1)N1Cc2cc(O)c(O)cc2C1] | 348.847 | $C_{17}H_{17}ClN_2O_2S$ | 349.2 |
| CIDD-0000032 | 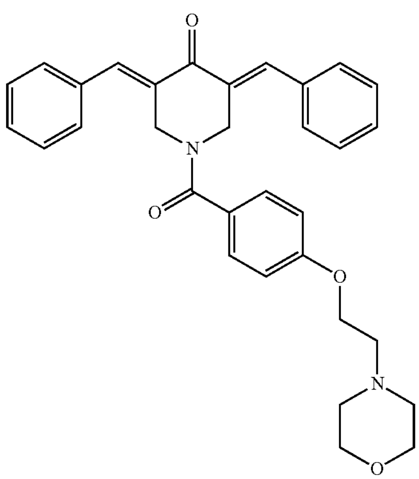 [SMILES: O=C1/C(=C/c2ccccc2)CN(C(=O)c2ccc(OCCN3CCOCC3)cc2)C/C1=C\c1ccccc1] | 508.608 | $C_{32}H_{32}N_2O_4$ | 509.5 |
| CIDD-0000036 | 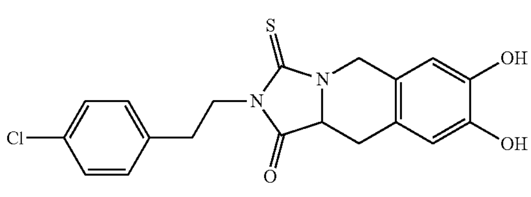 [SMILES: O=C1C2Cc3cc(O)c(O)cc3CN2C(=S)N1CCc1ccc(Cl)cc1] | 388.868 | $C_{19}H_{17}ClN_2O_3S$ | 389.2 |
| CIDD-0000037 | 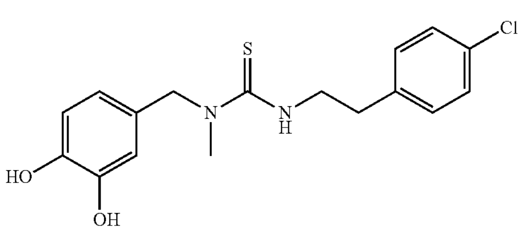 [SMILES: CN(Cc1ccc(O)c(O)c1)C(=S)NCCc1ccc(Cl)cc1] | 350.863 | $C_{17}H_{19}ClN_2O_2S$ | 351.2 |

TABLE 2-continued

Compounds with Characterization Data

| Molecule Name | Structure | MW | Chemical formula | Observed MS m/z (m + 1) |
|---|---|---|---|---|
| CIDD-0000056 | 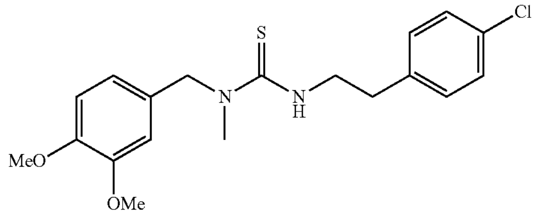 [SMILES: COc1ccc(CN(C)C(=S)NCCc2ccc(Cl)cc2)cc1OC] | 378.916 | $C_{19}H_{23}ClN_2O_2S$ | 379.3 |
| CIDD-0000057 | 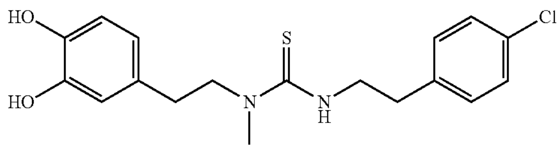 | 364.89 | $C_{18}H_{21}ClN_2O_2S$ | 365.3 |
| CIDD-0000058 | 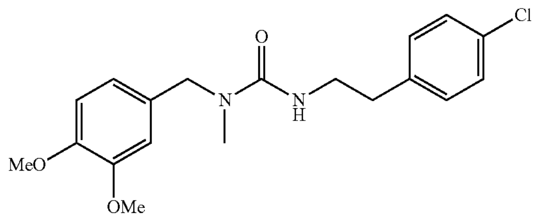 | 362.851 | $C_{19}H_{23}ClN_2O_3$ | 363.3 |
| CIDD-0000059 | 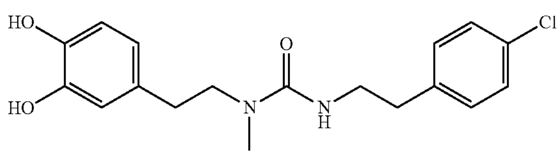 [SMILES: CN(CCc1ccc(O)c(O)c1)C(=S)NCCc1ccc(Cl)cc1] | 348.824 | $C_{18}H_{21}ClN_2O_3$ | 349.3 |
| CIDD-0000060 | 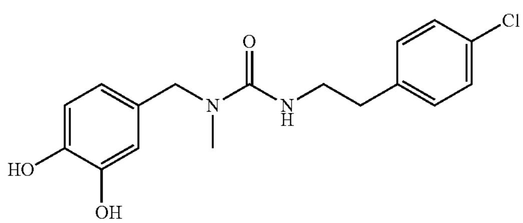 | 334.797 | $C_{17}H_{19}ClN_2O_3$ | 335.3 |
| CIDD-0000093 | 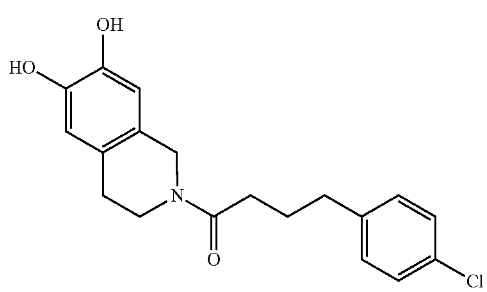 [SMILES: O=C(CCCc1ccc(Cl)cc1)N1CCc2cc(O)c(O)cc2C1] | 345.82 | $C_{19}H_{20}ClNO_3$ | 346.2 |
| CIDD-0000094 | 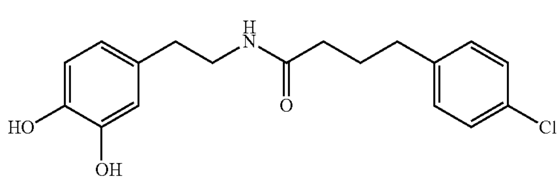 [SMILES: O=C(CCCc1ccc(Cl)cc1)NCCc1ccc(O)c(O)c1] | 333.809 | $C_{18}H_{20}ClNO_3$ | 334.2 |

TABLE 2-continued

Compounds with Characterization Data

| Molecule Name | Structure | MW | Chemical formula | Observed MS m/z (m + 1) |
|---|---|---|---|---|
| CIDD-0000097 | 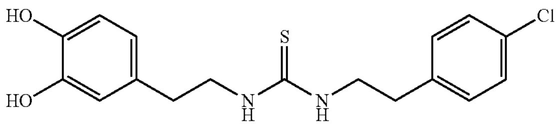 [SMILES: Oc1ccc(CCNC(=S)NCCc2ccc(Cl)cc2)cc1O] | 350.863 | $C_{17}H_{19}ClN_2O_2S$ | 351.1 |
| CIDD-0000098 | 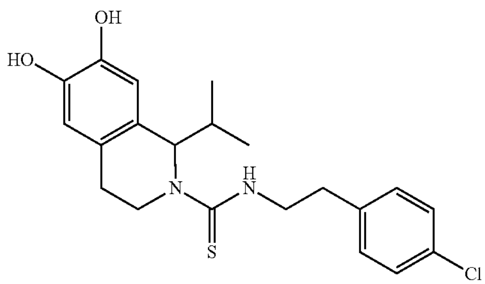 [SMILES: CC(C)C1c2cc(O)c(O)cc2CCN1C(=S)NCCc1ccc(Cl)cc1] | 404.953 | $C_{21}H_{25}ClN_2O_2S$ | 405.2 |
| CIDD-0000099 | 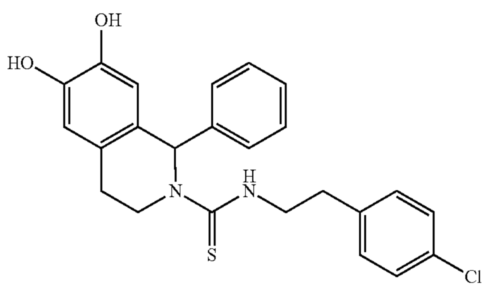 [SMILES: Oc1cc2c(cc1O)C(c1ccccc1)N(C(=S)NCCc1ccc(Cl)cc1)CC2] | 438.97 | $C_{24}H_{23}ClN_2O_2S$ | 439.1 |
| CIDD-0000100 | 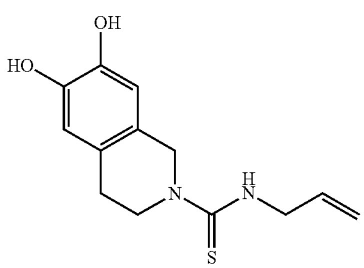 [SMILES: C=CCNC(=S)N1CCc2cc(O)c(O)cc2C1] | 264.343 | $C_{13}H_{16}N_2O_2S$ | 265.1 |
| CIDD-0000103 | 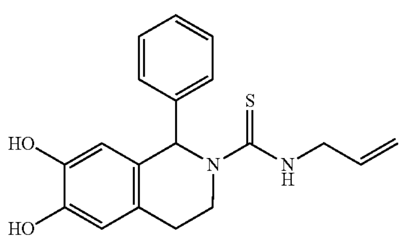 [SMILES: C=CCNC(=S)N1CCc2cc(O)c(O)cc2C1c1ccccc1] | 340.439 | $C_{19}H_{20}N_2O_2S$ | 341.2 |
| CIDD-0000104 | 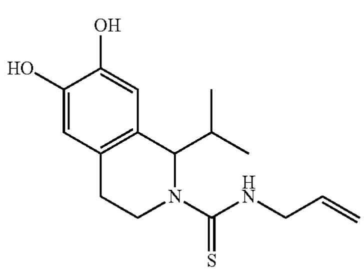 [SMILES: C=CCNC(=S)N1CCc2cc(O)c(O)cc2C1C(C)C] | 306.423 | $C_{16}H_{22}N_2O_2S$ | 307.2 |

TABLE 2-continued

Compounds with Characterization Data

| Molecule Name | Structure | MW | Chemical formula | Observed MS m/z (m + 1) |
|---|---|---|---|---|
| CIDD-0000105 | 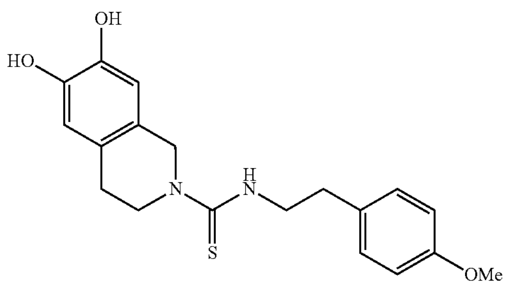 [SMILES: COc1ccc(CCNC(=S)N2CCc3cc(O)c(O)cc3C2)cc1] | 358.455 | $C_{19}H_{22}N_2O_3S$ | 359.2 |
| CIDD-0000106 | 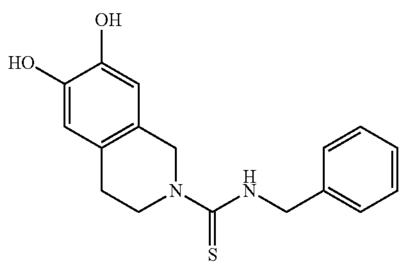 [SMILES: Oc1cc2c(cc1O)CN(C(=S)NCc1ccccc1)CC2] | 314.402 | $C_{17}H_{18}N_2O_2S$ | 315.1 |
| CIDD-0000107 | 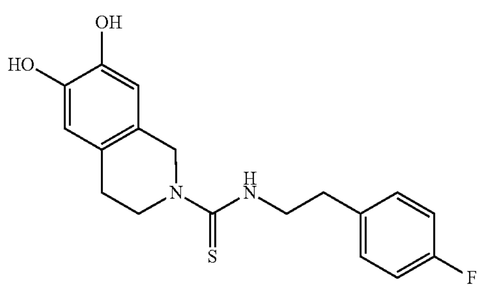 [SMILES: Oc1cc2c(cc1O)CN(C(=S)NCCc1ccc(F)cc1)CC2] | 346.419 | $C_{18}H_{19}FN_2O_2S$ | 347.1 |
| CIDD-0000108 | 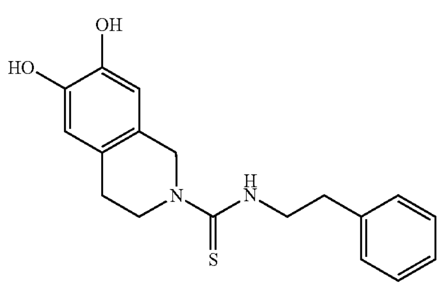 [SMILES: Oc1cc2c(cc1O)CN(C(=S)NCCc1ccccc1)CC2] | 328.429 | $C_{18}H_{20}N_2O_2S$ | 329.2 |
| CIDD-0000109 | 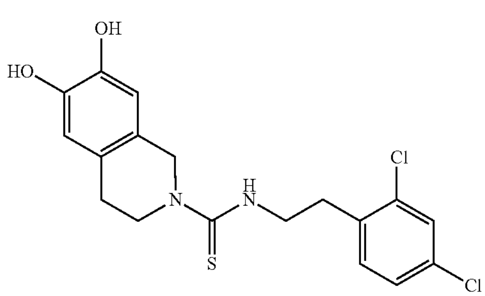 [SMILES: Oc1cc2c(cc1O)CN(C(=S)NCCc1ccc(Cl)cc1Cl)CC2] | 397.319 | $C_{18}H_{18}Cl_2N_2O_2S$ | 397.1 |

TABLE 2-continued

Compounds with Characterization Data

| Molecule Name | Structure | MW | Chemical formula | Observed MS m/z (m + 1) |
|---|---|---|---|---|
| CIDD-0000110 | 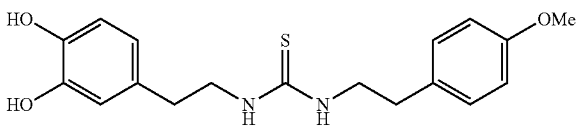 [SMILES: COc1ccc(CCNC(=S)NCCc2ccc(O)c(O)c2)cc1] | 346.444 | $C_{18}H_{22}N_2O_3S$ | 347.2 |
| CIDD-0000111 | 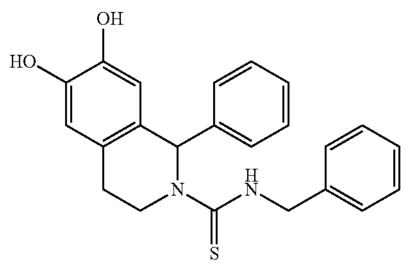 [SMILES: Oc1cc2c(cc1O)C(c1ccccc1)N(C(=S)NCc1ccccc1)CC2] | 390.498 | $C_{23}H_{22}N_2O_2S$ | 391.2 |
| CIDD-0000112 | 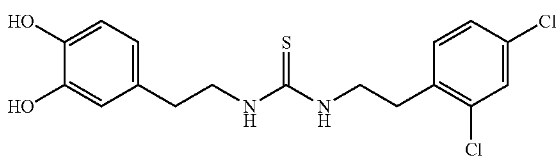 [SMILES: Oc1ccc(CCNC(=S)NCCc2ccc(Cl)cc2Cl)cc1O] | 385.308 | $C_{17}H_{18}Cl_2N_2O_2S$ | 385.1 |
| CIDD-0000113 | 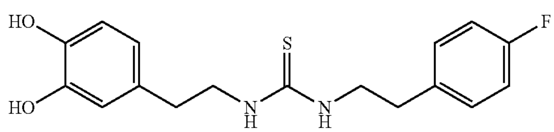 [SMILES: Oc1ccc(CCNC(=S)NCCc2ccc(F)cc2)cc1O] | 334.408 | $C_{17}H_{19}FN_2O_2S$ | 335.1 |
| CIDD-0000114 | 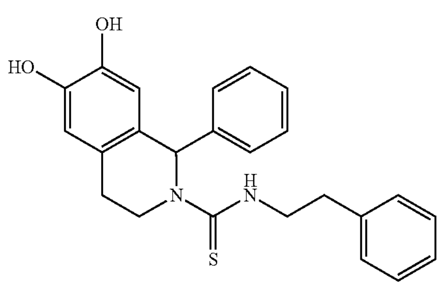 [SMILES: Oc1cc2c(cc1O)C(c1ccccc1)N(C(=S)NCCc1ccccc1)CC2] | 404.525 | $C_{24}H_{24}N_2O_2S$ | 405.2 |
| CIDD-0000115 | 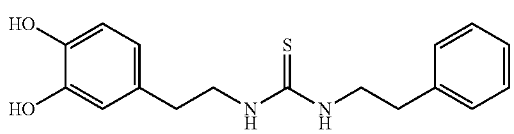 [SMILES: Oc1ccc(CCNC(=S)NCCc2ccccc2)cc1O] | 316.418 | $C_{17}H_{20}N_2O_2S$ | 317.2 |
| CIDD-0000116 | 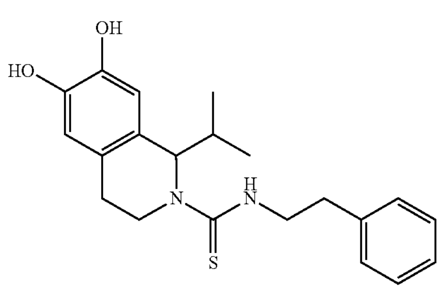 [SMILES: CC(C)C1c2cc(O)c(O)cc2CCN1C(=S)NCCc1ccccc1] | 370.508 | $C_{21}H_{26}N_2O_2S$ | 371.2 |

TABLE 2-continued

Compounds with Characterization Data

| Molecule Name | Structure | MW | Chemical formula | Observed MS m/z (m + 1) |
|---|---|---|---|---|
| CIDD-0000117 | 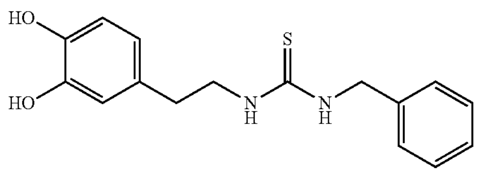 [SMILES: Oc1ccc(CCNC(=S)NCc2ccccc2)cc1O] | 302.391 | $C_{16}N_{18}N_2O_2S$ | 303.1 |
| CIDD-0000118 | 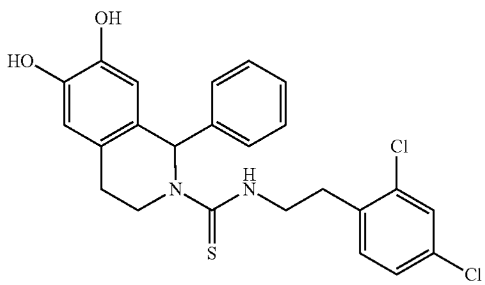 [SMILES: Oc1cc2c(cc1O)C(c1ccccc1)N(C(=S)NCCc1ccc(Cl)cc1Cl)CC2] | 473.415 | $C_{24}H_{22}Cl_2N_2O_2S$ | 473.1 |
| CIDD-0000123 | 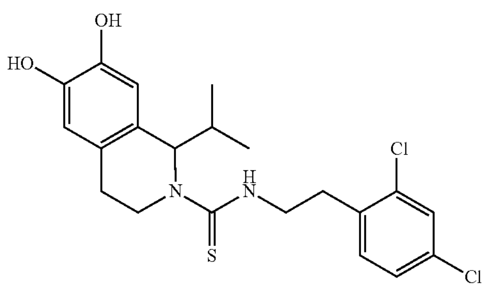 [SMILES: CC(C)C1c2cc(O)c(O)cc2CCN1C(=S)NCCc1ccc(Cl)cc1Cl] | 439.398 | $C_{21}H_{24}Cl_2N_2O_2S$ | 439.1 |
| CIDD-0000128 | 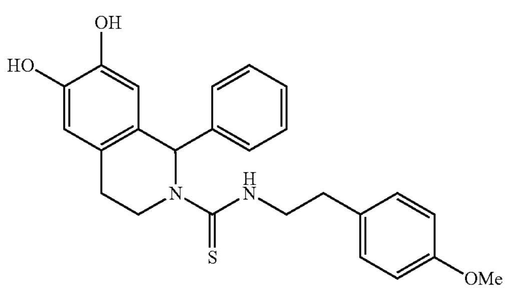 [SMILES: COc1ccc(CCNC(=S)N2CCc3cc(O)c(O)cc3C2c2ccccc2)cc1] | 434.551 | $C_{25}H_{26}N_2O_3S$ | 435.2 |
| CIDD-0000129 | 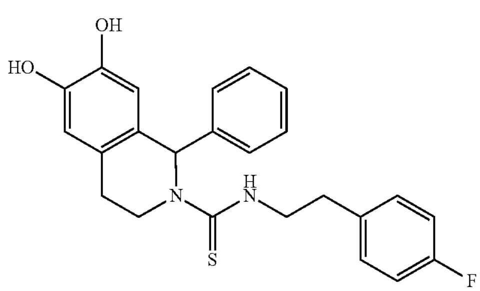 [SMILES: Oc1cc2c(cc1O)C(c1ccccc1)N(C(=S)NCCc1ccc(F)cc1)CC2] | 422.515 | $C_{24}H_{23}FN_2O_2S$ | 423.2 |

TABLE 2-continued

Compounds with Characterization Data

| Molecule Name | Structure | MW | Chemical formula | Observed MS m/z (m + 1) |
|---|---|---|---|---|
| CIDD-0000132 | 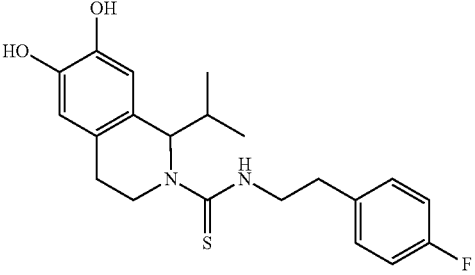 [SMILES: CC(C)C1c2cc(O)c(O)cc2CCN1C(=S)NCCc1ccc(F)cc1] | 388.499 | $C_{21}H_{25}FN_2O_2S$ | 389.2 |
| CIDD-0000133 | 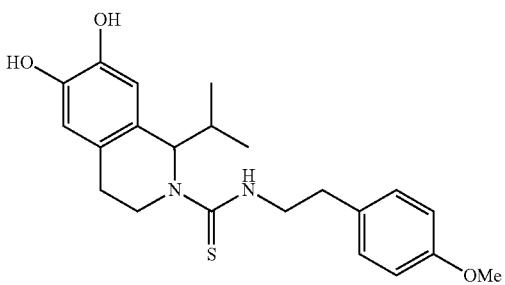 [SMILES: COc1ccc(CCNC(=S)N2CCc3cc(O)c(O)cc3C2C(C)C)cc1] | 400.534 | $C_{22}H_{28}N_2O_3S$ | 401.2 |
| CIDD-0000134 | 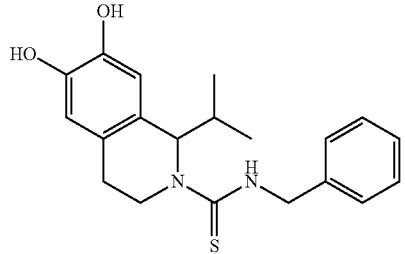 [SMILES: CC(C)C1c2cc(O)c(O)cc2CCN1C(=S)NCc1ccccc1] | 356.482 | $C_{20}H_{24}N_2O_2S$ | 357.2 |
| CIDD-0052319 | 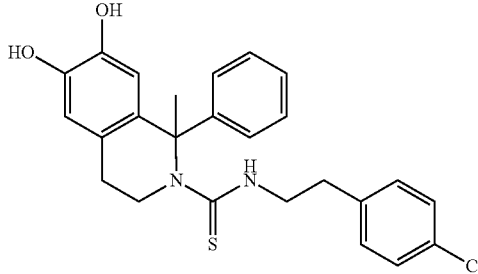 | 452.996 | $C_{25}H_{25}ClN_2O_2S$ | 453.2 |

2. Biological Analysis of Capsazepine Analogs

Figure 2:
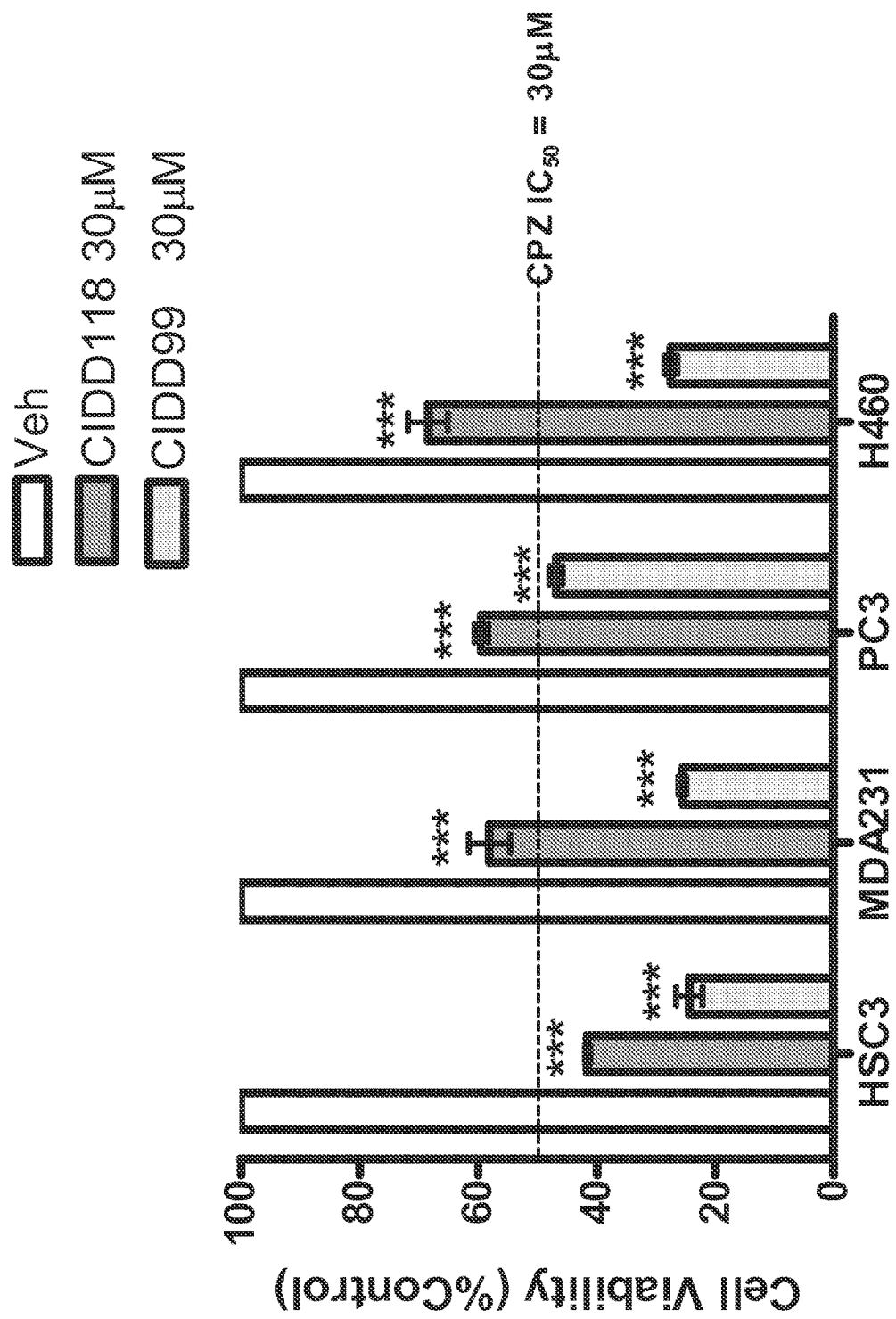
FIG. 2—Graph of cell viability for HSC3, MDA231, PC3, and H460 cell lines when treated with CIDD 99 or CIDD 118 for 24 hours compared to the vehicle. The inhibition of those cell lines with capsazepine is shown as a horizontal dashed line. ***p<0.001

In cell proliferation assays using OSCC cell lines (HSC3 and SCC4), the breast cancer cell line MDA231, and the prostate cancer cell line PC3, treatment with novel capsazepine analogs induces significant reduction (p<0.001) in cell proliferation following 24 hour treatments. This reduction can be seen in FIG. 1. The additional cell line data can be seen in FIGS. 2 and 3.

Figure 3:
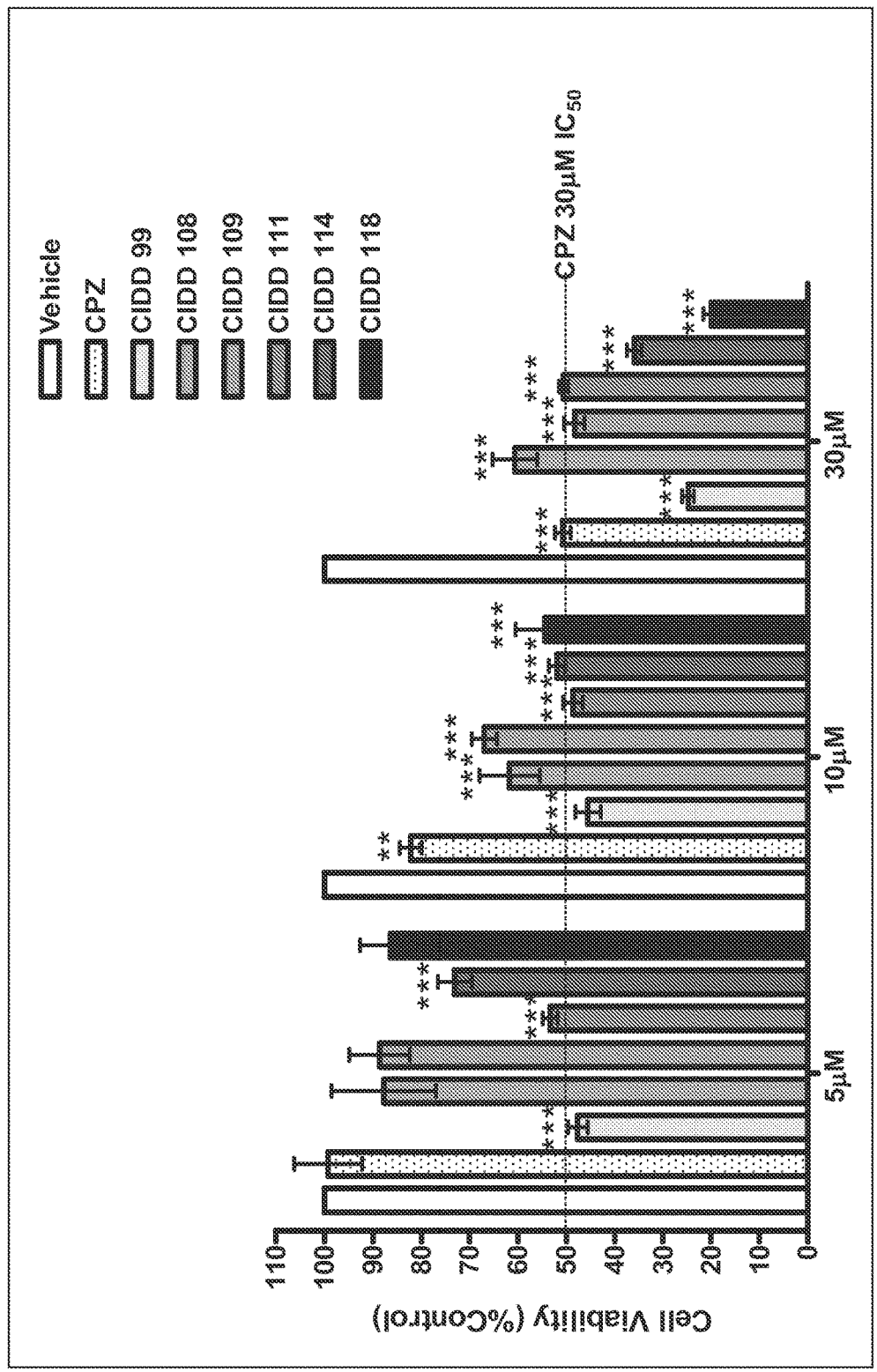
FIG. 3—Graph of cell viability for SCC4 cells treated with 5, 10, and 30 µM CIDD 99, 108, 109, 111, 114, or 118 for 24 hours compared to capsazepine and the vehicle. p<0.05 and *p<0.001.
Figure 4:
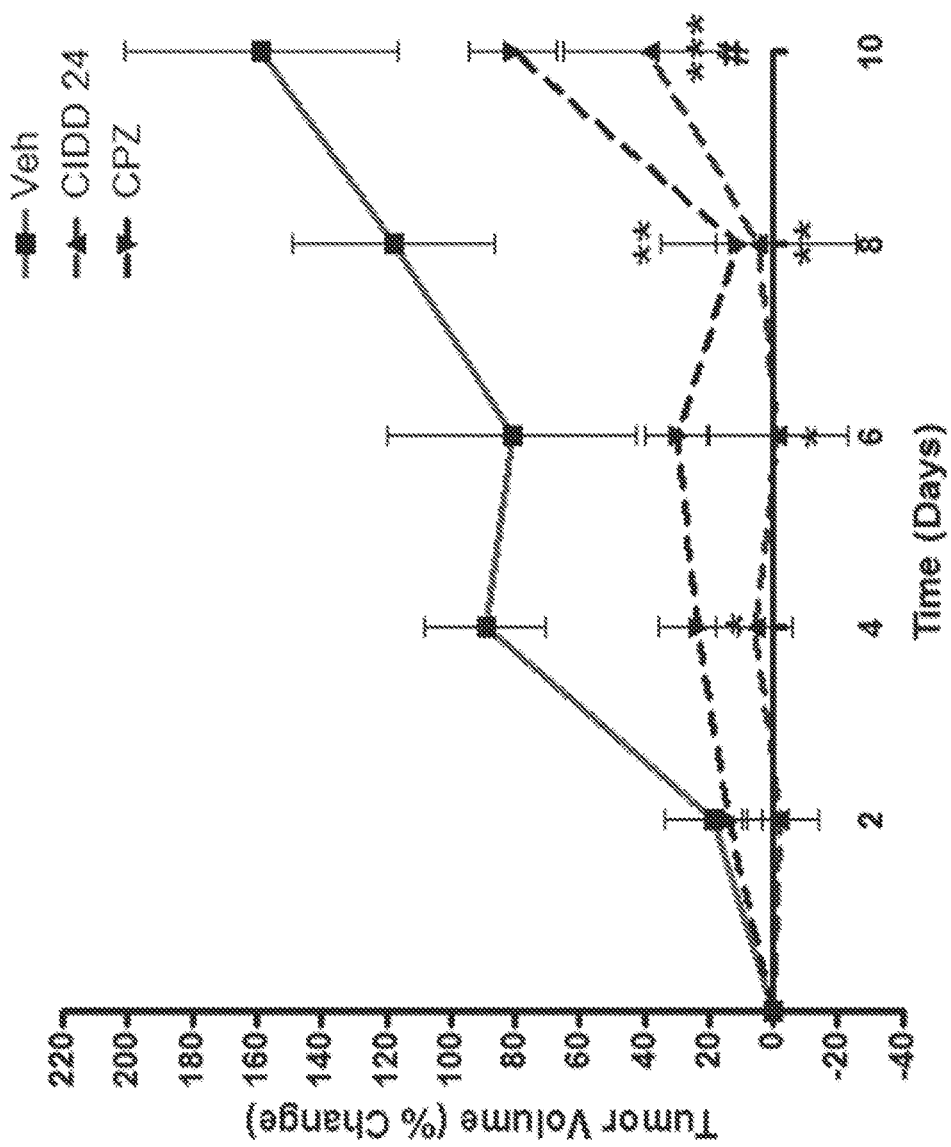
FIG. 4—Graph of tumor volumes % change of SCC4 xenografts after treatment with 40 µg (1 µg/µl) of CIDD 24 or capsazepine compared to the vehicle control over a 10 day period, n=5 per group. *p<0.05; p<0.01, and *p<0.001. CIDD 24 also shows a statistically significant difference between CIDD 24 and capsazepine (#=p<0.05).

In vivo testing was performed in OSCC xenografts generated in athymic nude mice inoculated with the OSCC cell line SCC4. The SCC4 tumors were treated with 40 gig of analog CIDD24, CIDD25, or capsazepine every other day for two weeks (FIG. 4). CIDD24 treatments yielded an 80% reduction in tumor growth in treated mice compared to vehicle control (p<0.01). CIDD25 yielded a 50% reduction in tumor growth compared to vehicle control, which is equivalent to the parent compound capsazepine (p<0.001, FIG. 4). Mice did not lose weight and they resumed normal motor function following each treatment and throughout the two week treatment period. No observable adverse effects on non-malignant adjacent tissue were seen. No erythema, swelling, or ulceration was detected. FIG. 3 and FIG. 4 showing graphical representation of cell proliferation assays with 9 analogs and in vivo pilot data with SCC4 xenografts treated with CIDD24 and CIDD25, respectively.

Figure 5:
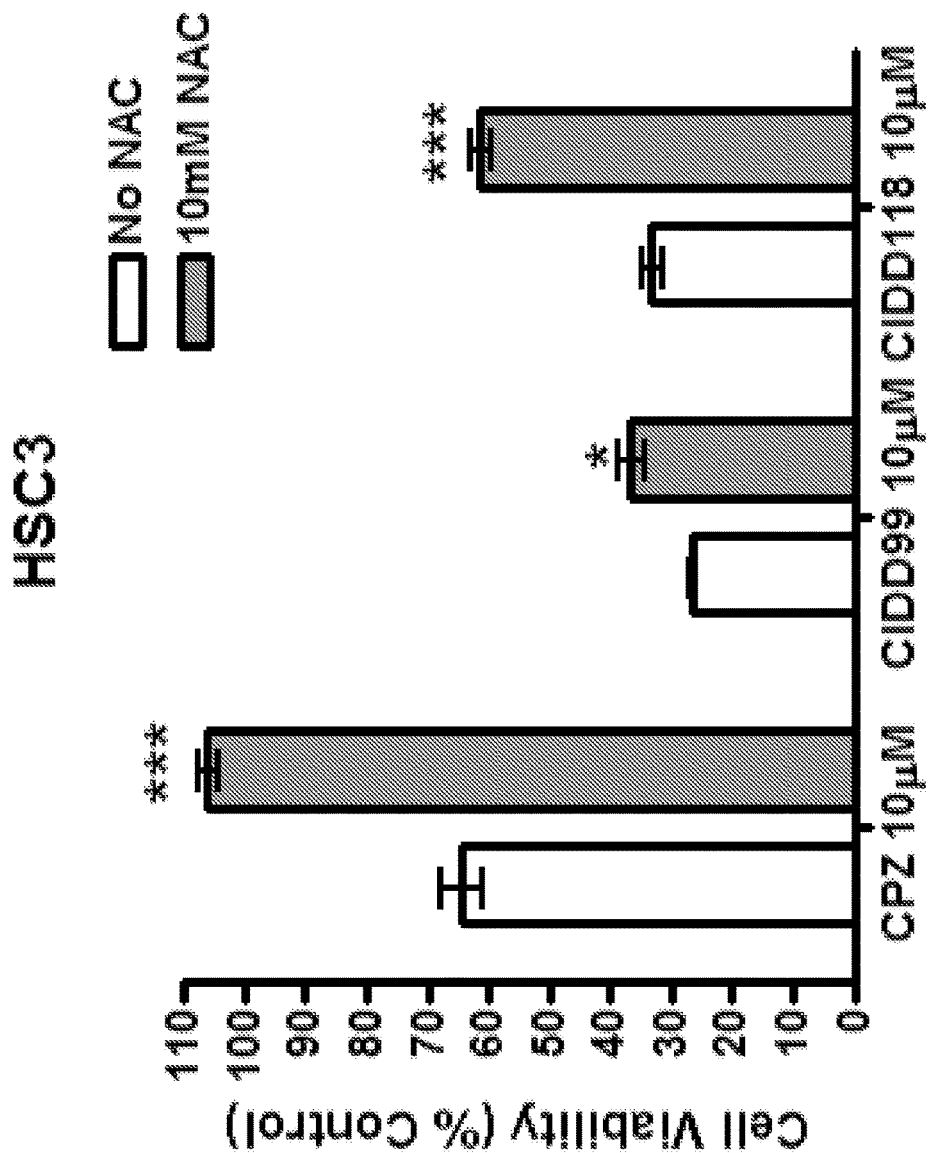
FIG. 5—Graph of cell viability for HSC3 cells when treated with capsazepine, CIDD 99, and CIDD 118 at 10 µM for 24 hours. The cell growth inhibition seen is reversed with 10 mM N-acetyl-cysteine is added to the cells. *p<0.05 and ***p<0.001.

Studies were undertaken to understand the mechanism of action for these compounds. When the cells were also treatment with the antioxidant N-acetyl-L-cysteine, the observed effects were reversed. Without being bound by theory, reversal of these effects indicating that these analogs are causing cell death by the production of reactive oxygen species (ROS). Flow cytometry analysis of cell cycle arrest following treatment of with analogs demonstrates that the cancer cells accumulate in the subG1 phase which is indicative of apoptosis. This reversal is shown in FIG. 5.

Figure 6:
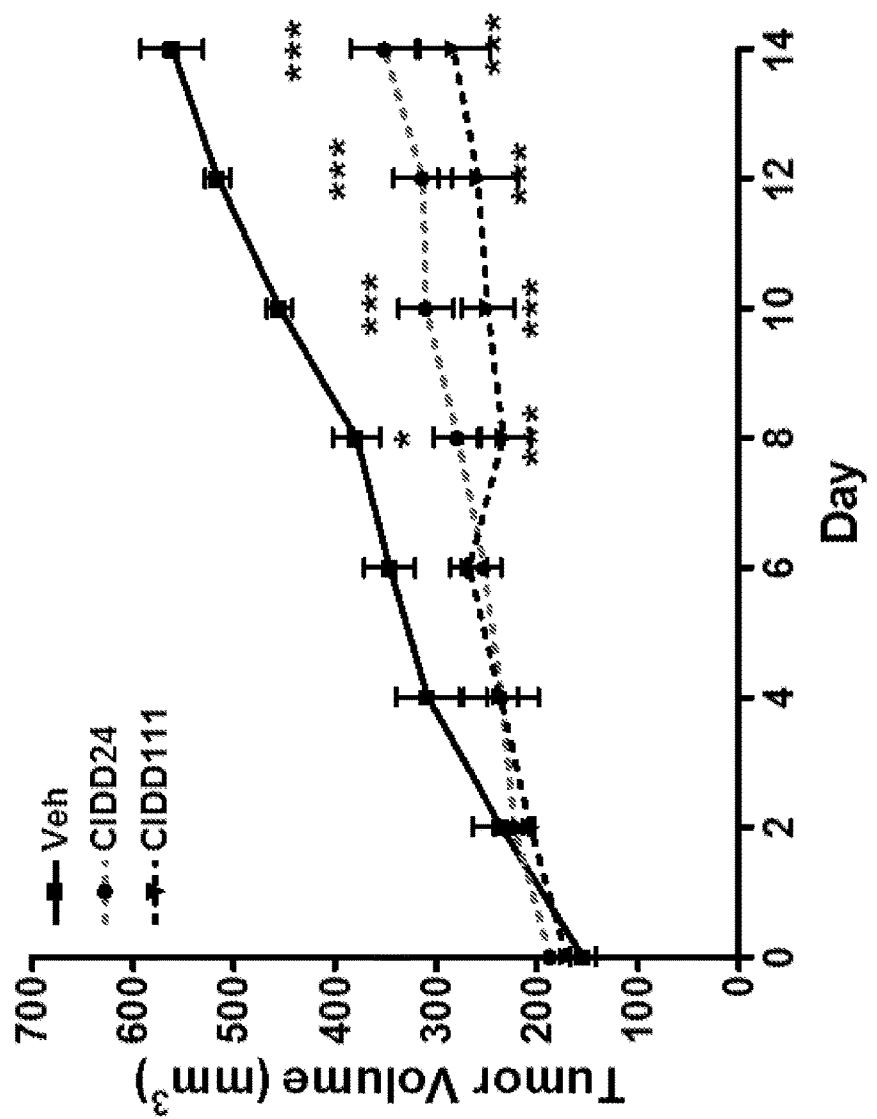
FIG. 6—Graph of SCC4 tumor volumes (mm$^3$) in mouse xenografts treated with 80 µg (1 µg/µl) of CIDD24, CIDD111, or vehicle control treated every other day for 14 days, n=5 per group. *p<0.05; *p<0.01, and ***p<0.001 compared to vehicle control.

Additional in vivo testing comparing efficacy of CIDD24 and CIDD111 in SCC4 tumors treated with 80 µg of capsazepine analog every other day for two weeks is shown in FIG. 6. Both CIDD24 and CIDD 111 yielded significant reduction in tumor growth (p<0.001) compared to vehicle control. Again, no adverse effects were observed. Although CIDD111 was slightly more effective than CIDD24, there was no significant difference in potency under these conditions.

3. Methods and Materials

Cell Lines.

OSCC cell lines, SCC4, SCC25, and HSC3 were derived from human primary tongue OSCC. SCC4 and SCC25 cells were obtained from ATCC (Rockville, Md.). HSC3 cells were kindly provided by Dr. Brian Schmidt (NYU) (Saghafi, et al., 2011). Breast cancer cells (MDA231), Prostate cancer cells (PC3), and Non-Small Cell Lung Cancer cells (H460) were obtained from ATCC (Rockville, Md.). Cells were maintained in DMEM (Gibco, Carlsbad, Calif.) containing 10% FBS at 37° C. in 5% $CO_2$. Immortalized keratinocytes (OKF6-TERT2; Harvard Medical School Cell Culture Core Collection, Cambridge, Mass.) were used as control epithelial cells.

Cell Viability Assays.

Cytotoxicity was assessed using the Cell Titer 96® Aqueous Non-Radioactive Cell Proliferation Assay (Promega, Madison, Wis.) according to manufacturer's protocol. Absorbance values of test groups were normalized against controls (n=4).

Reactive Oxygen Species (ROS) Assays.

ROS levels in OSCC cell lines were examined by flow cytometry using 2,7-dichlorodihydrofluorescein diacetate (DCF-DA; Sigma-Aldrich, St. Louis, Mo.). Cells (3×10$^5$) were plated in 12-well plates and incubated for 30 min with DCF-DA at 37° C. then treated with 30 µM of the appropriate capsazepine derivative or capsazepine using phenol free media with and without 10 mM NAC. Treated cells were incubated for 1 h at 37° C., harvested, washed twice, and analyzed by FACS.

Animals.

All studies were approved by the UTHSCSA Institutional Animal Care and Use Committee. Six week-old female athymic nude mice (Harlan, Indianapolis, Ind.) were used in a laminar air-flow cabinet under pathogen-free conditions. They were provided with a 12 h light/dark schedule at controlled temperature and humidity with food and water ad libitum. Mice were acclimated for one week prior to study initiation.

OSCC Mouse Xenograft Models.

Mice were injected subcutaneously in the right flank with 2×10$^6$ SCC4 cells in 0.1 mL of sterile PBS. Four weeks post-inoculation, tumors grew to an average volume of 150 mm$^3$. Mice were stratified into two experimental groups (n=5 per group), which received the following treatments as intra-tumor injections: group A, vehicle control; group B, capsazepine or capsazepine derivative (analog) treatment. Treatments were repeated every other day for a total of 14 days.

In Vivo Efficacy Analysis of Capsazepine Analogs in OSCC Xenograft Models.

Capsazepine and novel capsazepine analogs stock solutions (20 µg/µL, 100% Ethanol) were diluted to 5% Ethanol in sterile saline generating a final concentration of 1 µg/µL. SCC4 xenografts received intra-tumor injections of 40 µg CIDD24 or 40 µg capsazepine every other day (FIG. 4) for two weeks. In a second study SCC4 xenografts were injected with 80 µg CIDD24 or 80 µg CIDD111 every other day for two weeks (FIG. 5). Control xenografts received intra-tumor injections with vehicle control (5% Ethanol in sterile saline). Mice were monitored daily for tumor growth (using digital calipers), cachexia, and weight loss. Body temperature was monitored for 24 h following treatments. Tumor volumes were calculated by the elliptical formula: ½(Length× Width$^2$) (Jensen, et al., 2008).

Statistical Analysis.

Statistical analysis was performed using GraphPad Prism4 (San Diego, Calif.). Experiments were performed in triplicate and results are represented as means±SD except when indicated. Cytotoxicity assays of cell viability were analyzed by one-way ANOVA and Bonferroni's post hoc test (n=4). Statistical analyses of tumor growth were made using analysis of variance with repeated measures with Bonferroni's post hoc test (n=5). A p value less than 0.05 was considered statistically significant.

All of the compounds, formulations, and methods disclosed and claimed herein can be made and executed without undue experimentation in light of the present disclosure. While the compounds, formulations, and methods of this disclosure have been described in terms of preferred embodiments, it will be apparent to those of skill in the art that variations may be applied to the compounds, formulations, and methods, as well as in the steps or in the sequence of steps of the method described herein without departing from the concept, spirit, and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references to the extent that they provide exemplary procedural or other details supplementary to those set forth herein, are specifically incorporated herein by reference.

*Handbook of Pharmaceutical Salts: Properties, and Use*, Stahl and Wermuth Eds.), Verlag Helvetica Chimica Acta, 2002.

Jensen, et al., *BMC Med. Imaging*, 8:16, 2008

*March's Advanced Organic Chemistry: Reactions*, Mechanisms, and Structure, 2007.

Saghafi, et al., *Neurosci. Lett.*, 488:247-251, 2011.

WO 2014/089067

What is claimed:

1. A method of treating oral cancer comprising administering to a patient in need thereof a therapeutically effective amount of a compound of the formula:

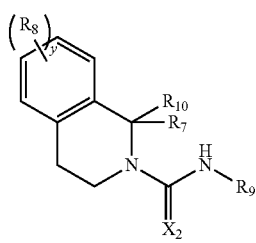

(II)

wherein:
X₂ is S;
R₇ is unsubstituted phenyl;
R₈ is —OH;
y is 2, 3, 4, 5, 6, 7, 8, or 9;
R₉ is aralkyl$_{(C≤12)}$, wherein the aryl ring is substituted with halogen; and
R₁₀ is hydrogen, alkyl$_{(C≤12)}$, or substituted alkyl$_{(C≤12)}$;
or a compound of the formula:

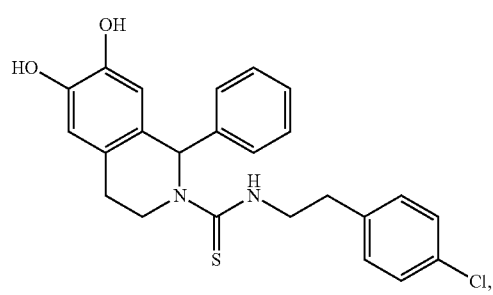 [SMILES: CC1(c2ccccc2)c2cc(O)c(O)cc2CCN1C(=S)NCCc1ccc(Cl)cc1]

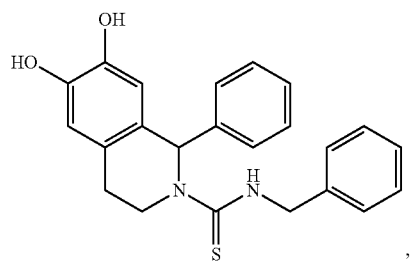

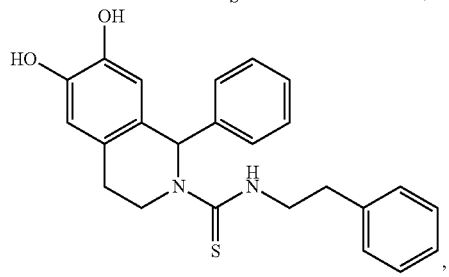

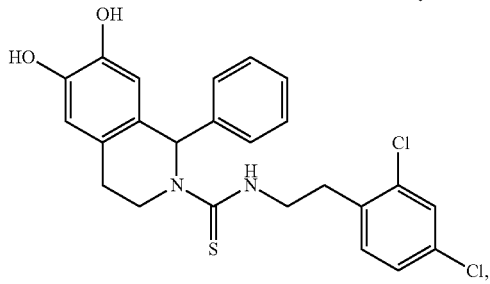

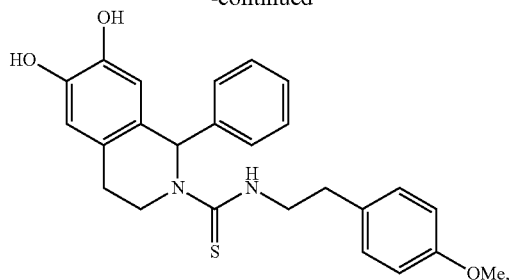

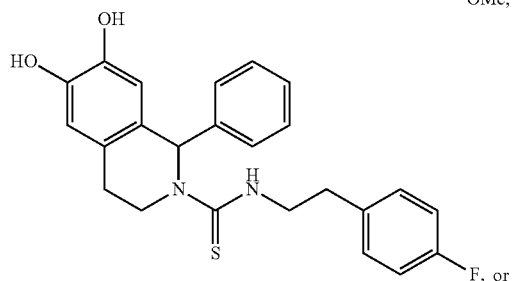

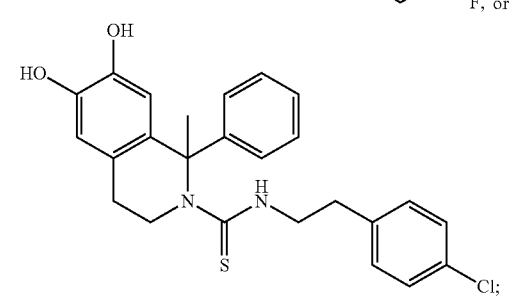

or a pharmaceutically acceptable salt or tautomer thereof.

2. The method according to claim 1, wherein the cancer is a carcinoma or a lymphoma.

3. The method of claim 1, wherein the cancer is inoperable.

4. The method of claim 3, wherein the inoperable cancer becomes operable after treatment with the compound.

5. The method according to claim 1, wherein the method comprises injecting the compound directly into the tumor or administering the compound systemically.

6. The method according to claim 1, wherein the method further comprises administering a pain therapy or a second cancer therapeutic regimen to said patient.

7. A compound of the formula:

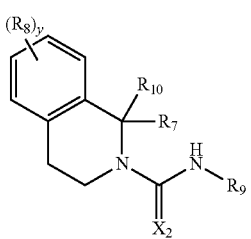

(II)

wherein:
X₂ is S;
R₇ is unsubstituted phenyl;
R₈ is —OH;
y is 2, 3, 4, 5, 6, 7, 8, or 9;
R₉ is aralkyl$_{(C≤12)}$, wherein the aryl ring is substituted with halogen; and $R_{10}$ is hydrogen, alkyl$_{(C\leq 12)}$, or substituted alkyl$_{(C\leq 12)}$; or a pharmaceutical salt or tautomer thereof.

8. A compound of the formula:

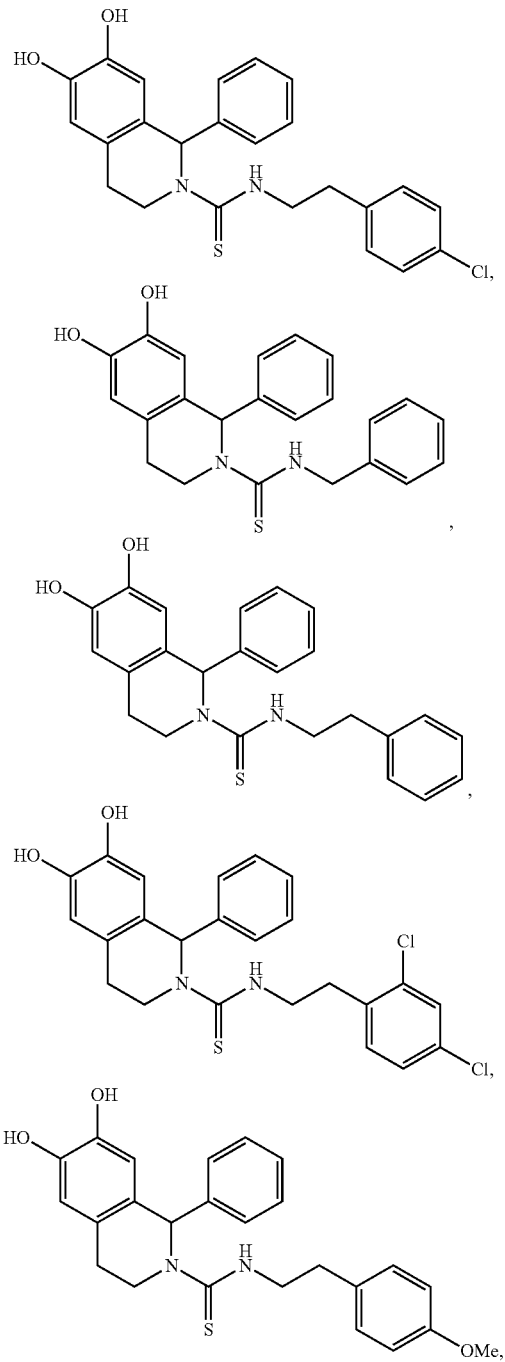

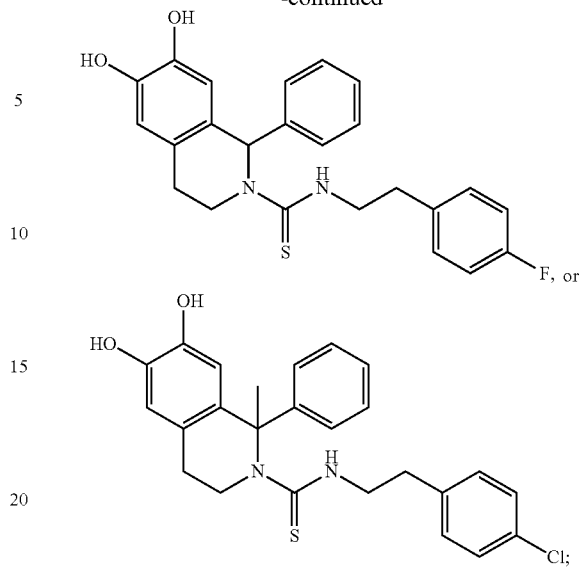

or a pharmaceutically acceptable salt or tautomer thereof.

9. The compound according to claim 7, wherein $R_{10}$ is alkyl$_{(C\leq 6)}$ or substituted alkyl$_{(C\leq 6)}$.

10. The compound according to claim 7, wherein y is 2, 3, or 4.

11. The method according to claim 1, wherein $R_{10}$ is alkyl$_{(C\leq 6)}$ or substituted alkyl$_{(C\leq 6)}$.

12. The method according to claim 1, wherein y is 2, 3, or 4.

13. The method according to claim 2, wherein the cancer is an oral squamous cell carcinoma.

14. The method according to claim 5, wherein the compound is formulated as an injectable solution.

15. The method according to claim 1, wherein the method comprises administering the compound systemically.

16. The method according to claim 14, wherein the compound is formulated for oral or intravenous administration.

17. The method according to claim 1, wherein the method further comprises alleviating pain.

18. The method according to claim 6, wherein the second therapeutic regimen is surgery, radiotherapy, immunotherapy, genetic therapy, or a second chemotherapeutic compound.

19. The method according to claim 18, wherein the second therapeutic regimen comprises metformin.

20. The method according to claim 1, wherein the compound reduces the tumor size such that the tumor becomes resectable.

* * * * *